(12) United States Patent
Hawes et al.

(10) Patent No.: US 12,127,592 B2
(45) Date of Patent: Oct. 29, 2024

(54) CAPSULE VALIDATION FOR HEAT-NOT-BURN (HNB) AEROSOL-GENERATING DEVICES

(71) Applicant: Altria Client Services LLC, Richmond, VA (US)

(72) Inventors: Eric Hawes, Richmond, VA (US); Zack W. Blackmon, Williamsburg, VA (US); Jarrett Keen, Richmond, VA (US); Rangaraj S. Sundar, Richmond, VA (US); Raymond W. Lau, Richmond, VA (US); Niall Gallagher, Cambridge (GB)

(73) Assignee: ALTRIA CLIENT SERVICES LLC, Richmond, VA (US)

( * ) Notice: Subject to any disclaimer, the term of this patent is extended or adjusted under 35 U.S.C. 154(b) by 415 days.

(21) Appl. No.: 17/479,274

(22) Filed: Sep. 20, 2021

(65) Prior Publication Data

US 2023/0087115 A1    Mar. 23, 2023

(51) Int. Cl.
A24F 40/46 (2020.01)
A24F 40/20 (2020.01)
(Continued)

(52) U.S. Cl.
CPC .............. *A24F 40/46* (2020.01); *A24F 40/20* (2020.01); *A24F 40/42* (2020.01); *A24F 40/53* (2020.01);
(Continued)

(58) Field of Classification Search
CPC .......... A24F 40/20; A24F 40/42; A24F 40/46; A24F 40/50; A24F 40/53; A24F 40/57;
(Continued)

(56) References Cited

U.S. PATENT DOCUMENTS

| 1,071,389 A | 8/1913 | Blosser |
| 1,934,887 A | 11/1933 | Robinson |

(Continued)

FOREIGN PATENT DOCUMENTS

| CN | 103945716 A | 7/2014 |
| CN | 203986136 U | 12/2014 |

(Continued)

OTHER PUBLICATIONS

International Search Report and Written Opinion dated Jan. 3, 2023.
Crafty Vaporizer manual (2014).

*Primary Examiner* — Abdullah A Riyami
*Assistant Examiner* — Thang H Nguyen
(74) *Attorney, Agent, or Firm* — Harness, Dickey & Pierce, P.L.C.

(57) ABSTRACT

A heater system for a non-combustible aerosol-generating device includes a heater element and a fuse element. The heater element has a heating region, a first terminal and a second terminal. The fuse element is electrically connected between the first terminal and the second terminal in parallel with the heater element. The fuse element has a region configured to induce a localized hot spot to cause the fuse element to open circuit in response to power applied between the first terminal and the second terminal.

25 Claims, 20 Drawing Sheets

(51) Int. Cl.
  *A24F 40/42* (2020.01)
  *A24F 40/53* (2020.01)
  *A24F 40/57* (2020.01)
  *A61M 11/00* (2006.01)
  *H05B 1/00* (2006.01)
  *A61M 11/04* (2006.01)

(52) U.S. Cl.
  CPC .............. *A24F 40/57* (2020.01); *H05B 1/00* (2013.01); *A61M 11/042* (2014.02); *A61M 2205/3653* (2013.01)

(58) Field of Classification Search
  CPC ............ A61M 11/042; A61M 15/0021; A61M 15/06; A61M 2205/18; A61M 2205/3368; A61M 2205/3592; A61M 2205/3653; A61M 2205/502; A61M 2205/505; A61M 2205/581; A61M 2205/582; A61M 2205/583; A61M 2205/6018; H01H 85/0241; H01H 85/10; H05B 1/00; H05B 1/0205; H05B 1/0252; H05B 2203/003; H05B 2203/022; H05B 3/04; H05B 3/06; H05B 3/24
  See application file for complete search history.

(56) References Cited

U.S. PATENT DOCUMENTS

| | | | |
|---|---|---|---|
| 4,214,146 A | 7/1980 | Schimanski |
| 4,564,748 A | 1/1986 | Gupton |
| 4,947,874 A | 8/1990 | Brooks et al. |
| 5,388,572 A | 2/1995 | Mulhauser et al. |
| 5,388,573 A | 2/1995 | Mulhauser et al. |
| 5,441,060 A | 8/1995 | Rose et al. |
| 5,460,173 A | 10/1995 | Mulhauser et al. |
| 5,593,792 A | 1/1997 | Farrier et al. |
| 5,619,984 A | 4/1997 | Hodson et al. |
| 5,645,050 A | 7/1997 | Zierenberg et al. |
| 5,665,262 A | 9/1997 | Hajaligol et al. |
| 5,823,182 A | 10/1998 | Van Oort |
| 6,006,747 A | 12/1999 | Eisele et al. |
| 6,065,472 A | 5/2000 | Anderson et al. |
| 6,095,153 A | 8/2000 | Kessler et al. |
| 6,481,437 B1 | 11/2002 | Pate |
| 7,186,958 B1 | 3/2007 | Nelson |
| 7,997,280 B2 | 8/2011 | Rosenthal |
| 8,488,952 B2 | 7/2013 | Landry |
| 8,490,627 B2 | 7/2013 | Levin et al. |
| 8,714,150 B2 | 5/2014 | Alelov |
| 8,910,630 B2 | 12/2014 | Todd |
| 9,072,322 B2 | 7/2015 | Liu |
| 9,549,573 B2 | 1/2017 | Monsees et al. |
| 9,693,587 B2 | 7/2017 | Plojoux et al. |
| 9,756,876 B2 | 9/2017 | Liu |
| 9,775,379 B2 | 10/2017 | Davidson et al. |
| 9,943,114 B2 | 4/2018 | Batista |
| 9,980,522 B1 | 5/2018 | Heidl et al. |
| 9,986,767 B2 | 6/2018 | Batista et al. |
| 9,999,258 B2 | 6/2018 | Newcomb et al. |
| 10,015,990 B2 | 7/2018 | Mironov |
| 10,031,183 B2 | 7/2018 | Novak, III et al. |
| 10,045,567 B2 | 8/2018 | Monsees et al. |
| 10,058,129 B2 | 8/2018 | Monsees et al. |
| 10,058,130 B2 | 8/2018 | Monsees et al. |
| 10,064,432 B2 | 9/2018 | Hawes et al. |
| 10,076,139 B2 | 9/2018 | Monsees et al. |
| 10,099,020 B2 | 10/2018 | Davidson et al. |
| 10,104,913 B2 | 10/2018 | Lau et al. |
| 10,111,470 B2 | 10/2018 | Monsees et al. |
| 10,130,124 B2 | 11/2018 | Wong et al. |
| 10,149,498 B2 | 12/2018 | Batista et al. |
| 10,172,390 B2 | 1/2019 | Nakano et al. |
| 10,179,215 B2 | 1/2019 | Raichman |
| 10,201,190 B2 | 2/2019 | Monsees et al. |
| D843,649 S | 3/2019 | Rasmussen et al. |
| 10,219,543 B2 | 3/2019 | Gill et al. |
| 10,247,443 B2 | 4/2019 | Flick |
| 10,251,423 B2 | 4/2019 | Mamoun et al. |
| 10,271,578 B2 | 4/2019 | John et al. |
| 10,278,424 B2 | 5/2019 | Garthaffner et al. |
| 10,292,436 B2 | 5/2019 | Cirillo et al. |
| 10,314,343 B2 | 6/2019 | Newcomb et al. |
| 10,321,716 B2 | 6/2019 | Zitzke |
| 10,328,443 B2 | 6/2019 | Ricketts et al. |
| 10,433,585 B2 | 10/2019 | Tucker et al. |
| 10,485,269 B2 | 11/2019 | Hawes et al. |
| D870,368 S | 12/2019 | Leon Duque et al. |
| 10,492,529 B2 | 12/2019 | Borkovec et al. |
| 10,524,512 B2 | 1/2020 | Sebastian et al. |
| 10,555,560 B2 | 2/2020 | Bilat et al. |
| 10,588,357 B2 | 3/2020 | Hawes et al. |
| 10,602,776 B2 | 3/2020 | Batista |
| 10,624,394 B2 | 4/2020 | Memari et al. |
| 10,645,971 B2 | 5/2020 | Zitzke |
| 10,667,557 B2 | 6/2020 | Mironov et al. |
| 10,667,560 B2 | 6/2020 | Atkins et al. |
| 10,674,770 B2 | 6/2020 | Talon |
| 10,701,975 B2 | 7/2020 | Bowen et al. |
| 10,701,981 B2 | 7/2020 | Newcomb et al. |
| 10,709,173 B2 | 7/2020 | Monsees et al. |
| 10,721,967 B2 | 7/2020 | Raichman |
| D893,096 S | 8/2020 | Leon Duque et al. |
| 10,757,972 B2 | 9/2020 | Matsumoto et al. |
| 10,757,975 B2 | 9/2020 | Batista et al. |
| 10,765,821 B2* | 9/2020 | Raichman ................ A24D 1/20 |
| 10,772,354 B2 | 9/2020 | Batista |
| 10,905,835 B2 | 2/2021 | Atkins et al. |
| 2004/0159322 A1 | 8/2004 | Kladders et al. |
| 2005/0063686 A1 | 3/2005 | Whittle et al. |
| 2007/0045288 A1 | 3/2007 | Nelson |
| 2007/0102013 A1 | 5/2007 | Adams et al. |
| 2008/0073558 A1 | 3/2008 | Howell et al. |
| 2009/0293888 A1 | 12/2009 | Williams et al. |
| 2009/0293892 A1 | 12/2009 | Williams et al. |
| 2010/0012118 A1 | 1/2010 | Storz |
| 2010/0059070 A1 | 3/2010 | Potter et al. |
| 2010/0078022 A1 | 4/2010 | Striebig et al. |
| 2010/0139655 A1 | 6/2010 | Genosar et al. |
| 2010/0313901 A1 | 12/2010 | Fernando et al. |
| 2011/0126848 A1 | 6/2011 | Zuber et al. |
| 2011/0192399 A1 | 8/2011 | Wilke et al. |
| 2012/0304990 A1 | 12/2012 | Todd |
| 2012/0325227 A1 | 12/2012 | Robinson et al. |
| 2013/0032145 A1 | 2/2013 | Adler et al. |
| 2013/0186392 A1 | 7/2013 | Haartsen et al. |
| 2013/0233309 A1 | 9/2013 | Todd |
| 2013/0233312 A1 | 9/2013 | Cohn |
| 2013/0255702 A1 | 10/2013 | Griffith, Jr. et al. |
| 2013/0276799 A1 | 10/2013 | Davidson et al. |
| 2014/0041655 A1 | 2/2014 | Barron et al. |
| 2014/0060554 A1 | 3/2014 | Collett et al. |
| 2014/0186015 A1 | 7/2014 | Breiwa, III et al. |
| 2014/0217197 A1 | 8/2014 | Selby et al. |
| 2014/0238423 A1 | 8/2014 | Tucker et al. |
| 2014/0253144 A1* | 9/2014 | Novak, III ............. A24F 40/50 324/550 |
| 2014/0283856 A1* | 9/2014 | Xiang .................... A24F 40/50 131/329 |
| 2014/0299141 A1 | 10/2014 | Flick |
| 2014/0321837 A1 | 10/2014 | Flick |
| 2014/0345606 A1 | 11/2014 | Talon |
| 2014/0366609 A1 | 12/2014 | Beck et al. |
| 2015/0059747 A1 | 3/2015 | Von Schuckmann |
| 2015/0122274 A1* | 5/2015 | Cohen .................... A24F 40/40 131/328 |
| 2016/0021932 A1 | 1/2016 | Silvestrini et al. |
| 2016/0057811 A1 | 2/2016 | Alarcon et al. |
| 2016/0295922 A1 | 10/2016 | John et al. |
| 2016/0316817 A1 | 11/2016 | Liu |
| 2016/0324216 A1 | 11/2016 | Li et al. |
| 2016/0331913 A1 | 11/2016 | Bourque |
| 2016/0338410 A1 | 11/2016 | Batista et al. |
| 2016/0345630 A1 | 12/2016 | Mironov et al. |

(56) References Cited

U.S. PATENT DOCUMENTS

| | | |
|---|---|---|
| 2016/0366947 A1 | 12/2016 | Monsees et al. |
| 2017/0055584 A1 | 3/2017 | Blandino et al. |
| 2017/0071251 A1 | 3/2017 | Goch |
| 2017/0095624 A1 | 4/2017 | Davidson et al. |
| 2017/0119979 A1 | 5/2017 | Davidson et al. |
| 2017/0143042 A1 | 5/2017 | Batista et al. |
| 2017/0144827 A1 | 5/2017 | Batista |
| 2017/0164657 A1 | 6/2017 | Batista |
| 2017/0196262 A1 | 7/2017 | Brereton et al. |
| 2017/0231276 A1 | 8/2017 | Mironov et al. |
| 2017/0311648 A1 | 11/2017 | Gill et al. |
| 2017/0347711 A1 | 12/2017 | Litten et al. |
| 2018/0007960 A1 | 1/2018 | Suzuki et al. |
| 2018/0042302 A1 | 2/2018 | Robinson et al. |
| 2018/0077967 A1 | 3/2018 | Hatton et al. |
| 2018/0084831 A1 | 3/2018 | Mironov |
| 2018/0104214 A1 | 4/2018 | Raichman |
| 2018/0214645 A1 | 8/2018 | Reevell |
| 2018/0235279 A1 | 8/2018 | Wilke et al. |
| 2018/0242644 A1 | 8/2018 | Bessant et al. |
| 2018/0243520 A1 | 8/2018 | Johnson et al. |
| 2018/0295885 A1 | 10/2018 | Rojo-Calderon et al. |
| 2018/0361334 A1 | 12/2018 | Bahabri |
| 2018/0366293 A1* | 12/2018 | Pineda ............... H01H 85/143 |
| 2019/0046745 A1 | 2/2019 | Nettenstrom et al. |
| 2019/0098930 A1 | 4/2019 | Fallon et al. |
| 2019/0099561 A1 | 4/2019 | Nettenstrom |
| 2019/0117915 A1 | 4/2019 | Raichman |
| 2019/0166913 A1 | 6/2019 | Trzecieski |
| 2019/0174827 A1 | 6/2019 | Fernando et al. |
| 2019/0208823 A1 | 7/2019 | Raichman |
| 2019/0208826 A1 | 7/2019 | John et al. |
| 2019/0224430 A1 | 7/2019 | Raichman |
| 2019/0254348 A1 | 8/2019 | Garthaffner et al. |
| 2019/0350256 A1 | 11/2019 | Hejazi |
| 2020/0037669 A1 | 2/2020 | Bowen et al. |
| 2020/0054076 A1 | 2/2020 | Lau et al. |
| 2020/0077702 A1 | 3/2020 | Mishra et al. |
| 2020/0085099 A1 | 3/2020 | Soriano et al. |
| 2020/0120988 A1 | 4/2020 | Qiu |
| 2020/0214343 A1 | 7/2020 | Fursa |
| 2020/0229507 A1 | 7/2020 | Flora et al. |
| 2020/0229509 A1 | 7/2020 | Griscik et al. |
| 2020/0236997 A1 | 7/2020 | Mironov et al. |
| 2020/0245680 A1 | 8/2020 | Williams |
| 2020/0246563 A1 | 8/2020 | Raichman |
| 2020/0260785 A1 | 8/2020 | Bowen et al. |
| 2020/0281249 A1 | 9/2020 | Sebastian et al. |
| 2020/0281269 A1 | 9/2020 | Malgat et al. |
| 2020/0297030 A1 | 9/2020 | Newcomb et al. |
| 2020/0329773 A1 | 10/2020 | Habicht et al. |
| 2020/0352239 A1 | 11/2020 | Batista |
| 2020/0375254 A1 | 12/2020 | Mironov et al. |
| 2020/0390149 A1 | 12/2020 | Hepworth et al. |
| 2020/0405980 A1* | 12/2020 | Griscik ............... A24F 40/42 |
| 2021/0015148 A1 | 1/2021 | Shenton et al. |
| 2021/0015153 A1 | 1/2021 | Raichman |
| 2021/0022395 A1 | 1/2021 | Moloney |
| 2022/0225672 A1 | 7/2022 | Hawes et al. |

FOREIGN PATENT DOCUMENTS

| | | |
|---|---|---|
| CN | 104349687 A | 2/2015 |
| CN | 204518097 U | 7/2015 |
| CN | 110200329 A | 9/2019 |
| EP | 0525720 A1 | 2/1993 |
| EP | 1007124 A1 | 6/2000 |
| EP | 1029451 A1 | 8/2000 |
| EP | 1385595 A2 | 2/2004 |
| EP | 1504768 A1 | 2/2005 |
| EP | 2468118 A1 | 6/2012 |
| EP | 3033953 A1 | 6/2016 |
| EP | 3100622 A1 | 12/2016 |
| EP | 3166425 B1 | 6/2018 |
| EP | 3430921 A1 | 1/2019 |
| EP | 3435798 A1 | 2/2019 |
| EP | 3313212 B1 | 4/2019 |
| EP | 3498115 A1 | 6/2019 |
| EP | 3504989 A1 | 7/2019 |
| EP | 3528592 A1 | 8/2019 |
| EP | 3539599 A1 | 9/2019 |
| EP | 3166429 B1 | 11/2019 |
| EP | 3068246 B1 | 4/2020 |
| EP | 3462932 B1 | 4/2020 |
| EP | 3166430 B1 | 9/2020 |
| EP | 3708011 A1 | 9/2020 |
| EP | 3711614 A1 | 9/2020 |
| EP | 3714714 A1 | 9/2020 |
| EP | 3232840 B1 | 11/2020 |
| EP | 3484315 B1 | 12/2020 |
| EP | 3508080 B1 | 1/2021 |
| EP | 3549464 B1 | 2/2021 |
| KR | 101319228 | 10/2013 |
| RU | 2536115 C2 | 12/2014 |
| WO | WO-2003/037306 A2 | 5/2003 |
| WO | WO-2014-146270 A1 | 9/2014 |
| WO | WO-2015/116934 A1 | 8/2015 |
| WO | WO-2015/117700 A1 | 8/2015 |
| WO | WO-2016/001921 A2 | 1/2016 |
| WO | WO-2016/001922 A1 | 1/2016 |
| WO | WO-2016/001923 A2 | 1/2016 |
| WO | WO-2016/001924 A2 | 1/2016 |
| WO | WO-2016/001925 A1 | 1/2016 |
| WO | WO-2016/001926 A1 | 1/2016 |
| WO | WO-2016/005533 A1 | 1/2016 |
| WO | WO-2016/10776 A1 | 1/2016 |
| WO | WO-2016/17244 A1 | 2/2016 |
| WO | WO-2016/026219 A1 | 2/2016 |
| WO | WO-2017/163045 A1 | 9/2017 |
| WO | WO-2018-53689 A1 | 3/2018 |
| WO | WO-2018/211252 A1 | 11/2018 |
| WO | WO-2018/217440 A1 | 11/2018 |
| WO | WO-2019/030115 A1 | 2/2019 |
| WO | WO-2019/46315 A1 | 3/2019 |
| WO | WO-2019/048880 A1 | 3/2019 |
| WO | WO-2019/068441 A1 | 4/2019 |
| WO | WO-2019/128551 A1 | 7/2019 |
| WO | WO-2019-134457 A1 | 7/2019 |
| WO | WO-2019/162497 A1 | 8/2019 |
| WO | WO-2019/162498 A1 | 8/2019 |
| WO | WO-2019/162500 A1 | 8/2019 |
| WO | WO-2019/162502 A1 | 8/2019 |
| WO | WO-2019/162503 A1 | 8/2019 |
| WO | WO-2019/162504 A1 | 8/2019 |
| WO | WO-2019/162506 A1 | 8/2019 |
| WO | WO-2019/162507 A1 | 8/2019 |
| WO | WO-2019/162508 A1 | 8/2019 |
| WO | WO-2019/200194 A1 | 10/2019 |
| WO | WO-2019/215039 A1 | 11/2019 |
| WO | WO-2019/224382 A1 | 11/2019 |
| WO | WO-2019/238819 A1 | 12/2019 |
| WO | WO-2020/025433 A1 | 2/2020 |
| WO | WO-2020/029923 A1 | 2/2020 |
| WO | WO-2020/056776 A1 | 3/2020 |
| WO | WO-2020-57474 A1 | 3/2020 |
| WO | WO-2020/089054 A1 | 5/2020 |
| WO | WO-2020/101198 A1 | 5/2020 |
| WO | WO-2020/115322 A1 | 6/2020 |
| WO | WO-2020/142003 A1 | 7/2020 |
| WO | WO-2020/210821 A1 | 10/2020 |
| WO | WO-2020/221815 A1 | 11/2020 |
| WO | WO-2020/223875 A1 | 11/2020 |
| WO | WO-2020/223876 A1 | 11/2020 |
| WO | WO-2020/264362 A1 | 12/2020 |
| WO | WO-2021/061360 A1 | 4/2021 |
| WO | WO-2021/262265 A1 | 12/2021 |

\* cited by examiner

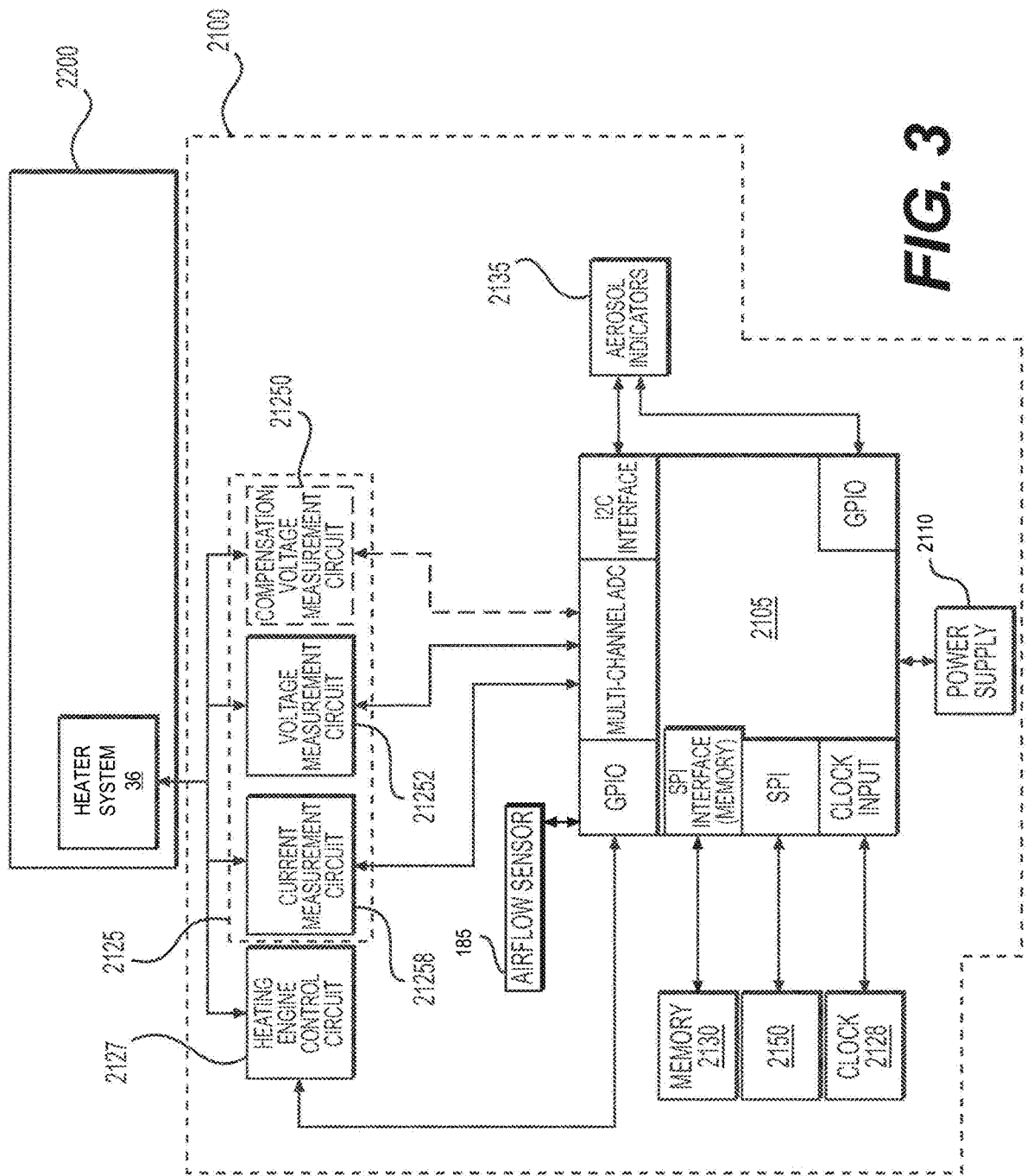

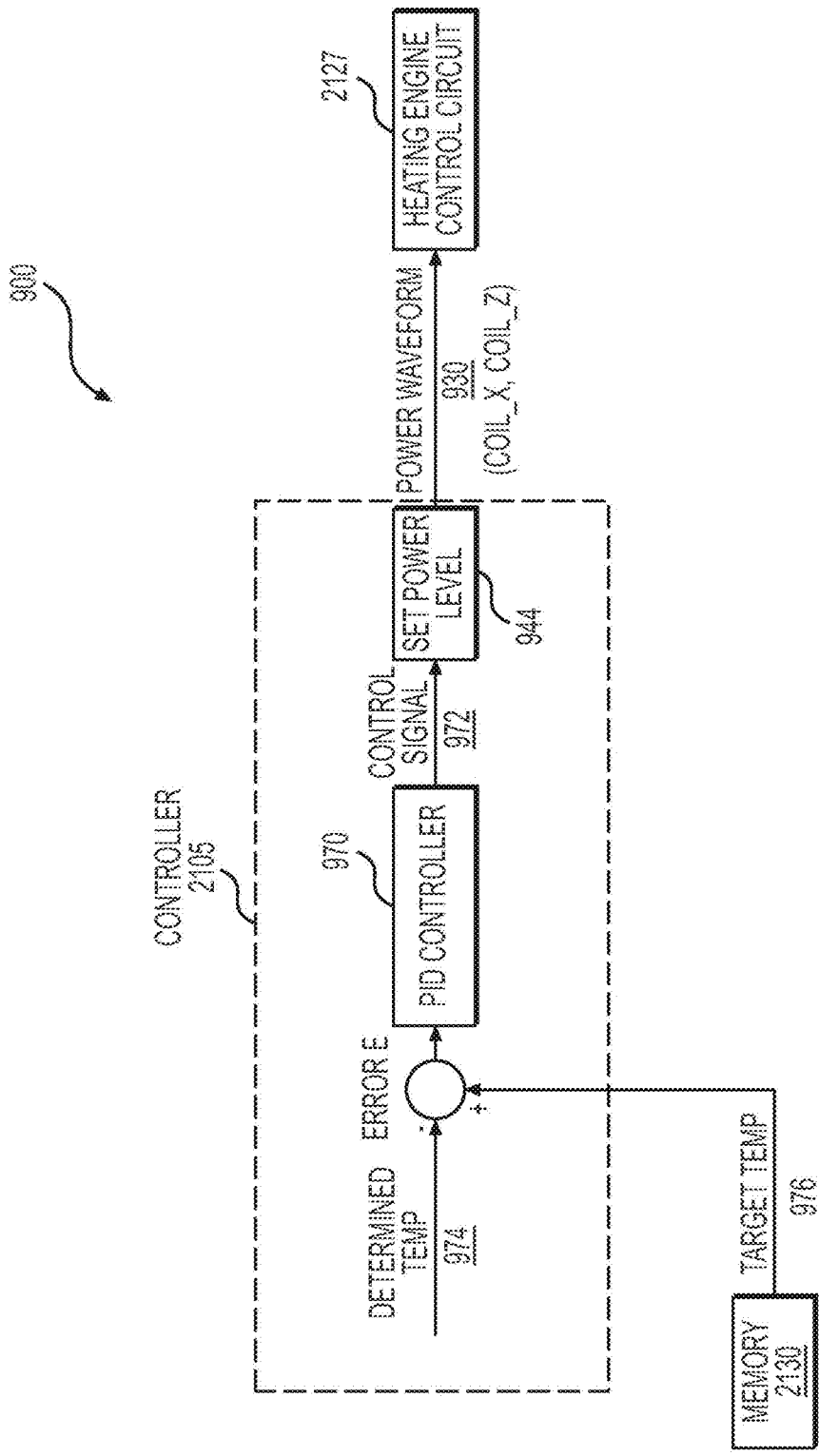

CAPSULE VALIDATION FOR HEAT-NOT-BURN (HNB) AEROSOL-GENERATING DEVICES

BACKGROUND

Field

The present disclosure relates to heat-not-burn (HNB) aerosol-generating devices, heaters for HNB aerosol-generating devices, capsules for HNB aerosol-generating devices, methods for capsule validation and/or identification, and/or methods of controlling HNB aerosol-generating devices.

Description of Related Art

Some electronic devices are configured to heat a plant material to a temperature that is sufficient to release constituents of the plant material while keeping the temperature below its ignition temperature so as to avoid a self-sustaining burning or a self-sustaining combustion of the plant material (i.e., in contrast to where a plant material is lit, such as lit-end cigarettes). Such devices may be characterized as generating an aerosol of constituents released by heating, and may be referred to as heat-not-burn aerosol-generating devices, or heat-not-burn devices.

SUMMARY

One or more example embodiments provide heat-not-burn (HnB) aerosol-generating devices that utilize a capsule including an integrated heater and an aerosol-forming substrate in (e.g., direct) contact with the integrated heater. The integrated heater may have a characteristic resistance, and may be fitted with a thermal fuse element (e.g., an integrated, non-resettable, thermal fuse) across the power terminals of the capsule such that the fuse element is connected in parallel with the resistance of the integrated heater.

According to at least some example embodiments, the heating control algorithm of the HnB device regulates the electrical power/energy delivered to the integrated heater during first application of power such that the fuse is blown (open-circuited) in a controlled way. The fusing profile (e.g., in terms of voltage, current and/or resistance) that results from application of a defined power profile (or waveform) may be assessed by the HnB device to, for example: identify the type of capsule, determine whether the capsule is a valid capsule and/or determine whether power has been previously applied to the capsule.

For example, the HnB device may identify capsule and/or determine whether the capsule is valid based on whether an observed resistance profile conforms to (or is within the bounds of) a known resistance profile envelope.

Since the fuse is only present prior to the first application of power to the heater, and is blown thereafter, the HnB device may determine whether power has been previously applied to the capsule based on an impedance check of the heater. If the measured (e.g., instantaneous) initial resistance matches the nominal resistance of the heater then the fuse is not present (open circuited) and the HnB device determines that power has been previously applied to the heater. At least one example embodiment provides a heater system for a non-combustible aerosol-generating device, the heater system comprising: a heater element having a heating region, a first terminal and a second terminal; and a fuse element electrically connected between the first terminal and the second terminal in parallel with the heater element, the fuse element having a region configured to induce a localized hot spot to cause the fuse element to open circuit in response to power applied between the first terminal and the second terminal.

According to at least some example embodiments, the fuse element may have a resistance enabling a heating power required to activate the fuse element to be passed through the heater system.

The region may be configured to induce a localized hot spot is a pinched or necked region.

The fuse element may be ultrasonically, electrically or laser spot welded between the first terminal and the second terminal.

The fuse element may be integral with the heater element.

The heater element may include a first extension region connecting the heating region with the first terminal, and a second extension region connecting the heating region with the second terminal. The fuse element may be electrically connected to the first extension region and the second extension region.

At least one example embodiment provides a capsule of a non-combustible aerosol-generating device, the capsule comprising: a housing containing an aerosol-forming substrate; a heater element arranged within the housing, the heater element having a first terminal, a second terminal and a heating region configured to heat the aerosol-forming substrate; and a fuse element electrically connected in parallel with the heater element, the fuse element having a region configured to induce a localized hot spot to cause the fuse element to open circuit in response to power applied between the first terminal and the second terminal.

The fuse element may have a resistance enabling a heating power required to activate the fuse element to be passed through the heater element and the fuse element.

The region may be configured to induce a localized hot spot is a pinched or necked region.

The fuse element may be ultrasonically, electrically or laser spot welded between the first terminal and the second terminal.

The fuse element may be integral with the heater element.

The housing may include a sleeve having a first end and a second end, a first end cap engaged with the first end, and a second end cap engaged with the second end. The second end cap may be molded around the first terminal, the second terminal and the fuse element.

The second end cap may include a chamber isolating the fuse element from air flow through the capsule.

The heater element may include a first extension region connecting the heating region with the first terminal, and a second extension region connecting the heating region with the second terminal. The fuse element may be electrically connected to the first extension region and the second extension region.

At least one other example embodiment provides a non-combustible aerosol-generating device comprising a capsule and a device body. The capsule includes: a heater element having a first terminal, a second terminal and a heating region configured to heat the aerosol-forming substrate; and a fuse element electrically connected in parallel with the heater element, the fuse element having a region configured to induce a localized hot spot to cause the fuse element to open circuit in response to power applied between the first terminal and the second terminal. The device body is configured to connect to the capsule, and includes: a power supply to provide power to the non-combustible aerosol-generating device; and a controller configured to control application of power to the heater element.

At least one other example embodiment provides a non-combustible aerosol-generating device comprising a capsule and a device body. The capsule includes a housing containing an aerosol-forming substrate, a heater element arranged in the housing, the heater element having a first terminal, a second terminal and a heating region configured to heat the aerosol-forming substrate, and a fuse element electrically connected between the first terminal and the second terminal. The device body is configured to connect to the capsule, and includes: a heating engine control circuit configured to apply power to the heater element, and a controller. The controller is configured to control the heating engine control circuit to apply a power waveform to the heater element, and to determine whether the capsule is valid based on a measured resistance profile for the heater element in response to the power waveform.

The non-combustible aerosol-generating device may further include a memory storing an expected resistance profile. The controller may be configured to determine whether the capsule is valid based on a comparison between the measured resistance profile and the expected resistance profile stored in the memory.

The controller may be configured to enable application of power to the heater element to heat the aerosol-forming substrate to generate aerosol in response to determining that the capsule is valid.

The controller may be configured to prevent application of power to the heater element to heat the aerosol-forming substrate to generate aerosol in response to determining that the capsule is not valid.

The controller may be configured to control the heating engine control circuit to apply the power waveform to the heater element, and to determine whether the capsule is valid prior to application of power to the heater element to heat the aerosol-forming substrate to generate aerosol.

The controller may be configured to obtain identification information for the capsule based on the measured resistance profile.

The non-combustible aerosol-generating device may further include a memory storing a plurality of expected resistance profiles. The controller may be configured to obtain the identification information for the capsule based on a comparison between the measured resistance profile and the plurality of expected resistance profiles stored in the memory.

The controller may be configured to determine aerosol-generating parameters for heating the aerosol-forming substrate based on the measured resistance profile.

The non-combustible aerosol-generating device may further include a memory storing a plurality of expected resistance profiles. The controller may be configured to determine the aerosol-generating parameters based on a comparison between the measured resistance profile and the plurality of expected resistance profiles stored in the memory.

The aerosol-generating parameters may include at least one of a heating power profile, a target temperature or a target resistance for heating the aerosol-forming substrate to generate aerosol.

A valid capsule may be at least one of an authentic capsule, a capsule that has not been damaged prior to insertion into the non-combustible aerosol-generating device, or a capsule having an intact fuse element.

BRIEF DESCRIPTION OF THE DRAWINGS

The various features and advantages of the non-limiting embodiments described herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

FIG. 3 illustrates electrical systems of an aerosol-generating device and a capsule according to example embodiments.

FIG. 8 illustrates a block diagram illustrating a temperature heating engine control algorithm according to at least some example embodiments.

DETAILED DESCRIPTION

Figure 1A:
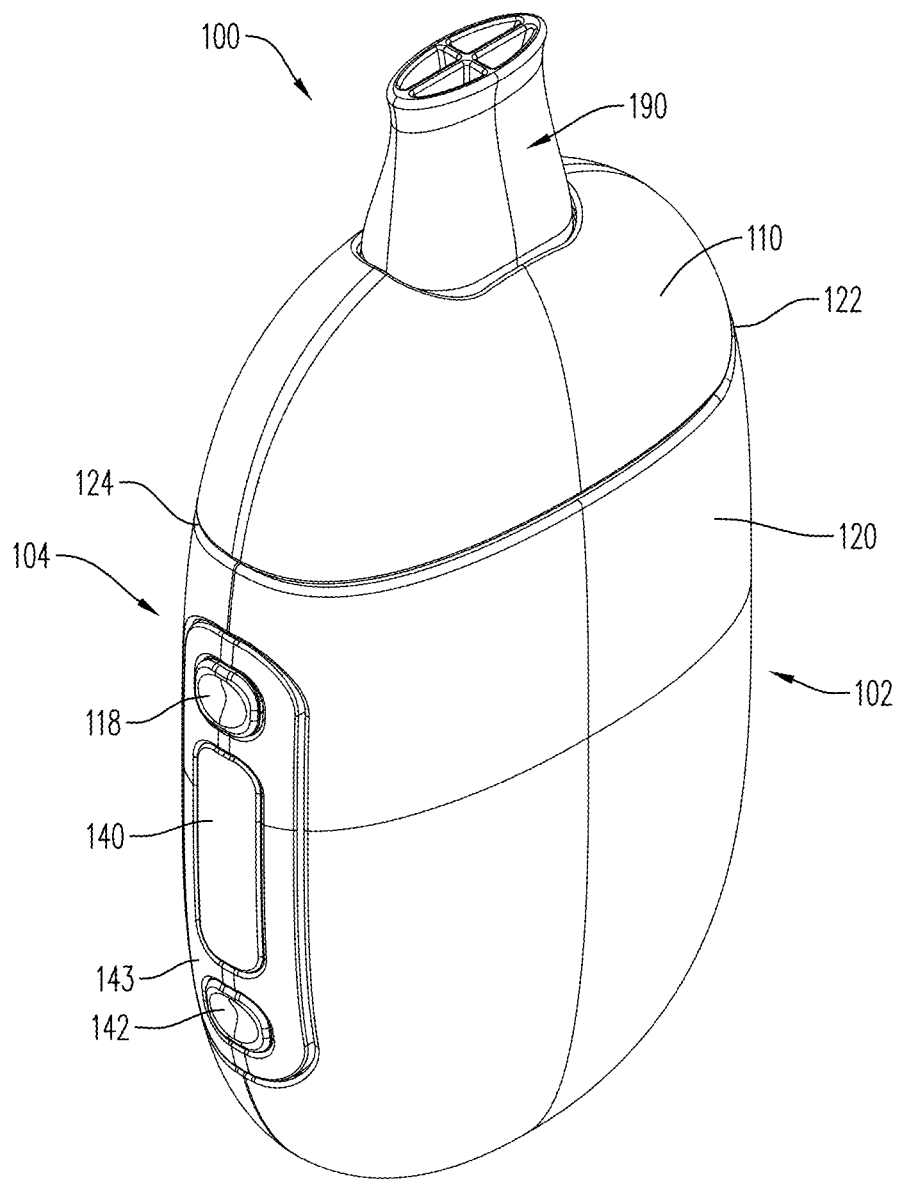
FIGS. 1A-1D illustrate various perspective views of an aerosol-generating device according to one or more example embodiments.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," or "covering" another element or layer, it may be directly on, connected to, coupled to, attached to, adjacent to or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements, and/or groups thereof.

When the words "about" and "substantially" are used in this specification in connection with a numerical value, it is intended that the associated numerical value include a tolerance of ±10% around the stated numerical value, unless otherwise explicitly defined.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

One or more example embodiments provide aerosol-generating devices including heater elements and precision heater control electronics enabling integration and/or utilization of electrically activated fusing elements to determine validity of a capsule, identify a capsule, and/or determine aerosol-generating parameters for the capsule upon being inserted into the aerosol-generating device.

One or more example embodiments may utilize a one-time fuse element within the capsule. The one-time fuse element within the capsule may enable detection of a shape (e.g., an exact shape) of a resistance profile required to activate (e.g., open-circuit) the fuse element, and a comparison of the resistance profile to one or more envelopes of acceptable resistance profiles to determine validity.

The one-time fuse element may also provide the ability to detect the shape (e.g., exact shape) of the fusing profile required to activate (e.g., blow or open-circuit) the fuse element, and to compare the detected fusing profile with a library of fusing profiles to determine the type of capsule inserted into the aerosol-generating device (e.g., a SKU, type of aerosol-forming substrate or material in the capsule, or the like), and/or aerosol-generating parameters for heating the aerosol-generating substrate in the capsule.

The one-time fuse element may also provide the ability to detect whether a fuse is intact, which may indicate whether the capsule has been previously inserted into the aerosol-generating device and/or whether the aerosol-generating substrate in the capsule has been previously heated.

FIGS. 1A-1D are illustrations of an aerosol-generating device 100 (e.g., heat-not-burn (HNB) aerosol-generating device) in accordance with at least one example embodiment. For example, FIG. 1A is a top perspective view of the aerosol-generating device 100, where the lid 110 is closed. FIG. 1B is a bottom perspective view of the aerosol-generating device 100, where the lid 110 is closed. FIG. 1C is a bottom-up view of the aerosol-generating device 100, where the lid 110 is closed. FIG. 1D is another top perspective view of the aerosol-generating device 100, where the lid 110 is opened and a capsule 200 is received by the capsule-receiving cavity 130.

As illustrated, in at least some example embodiments, the aerosol-generating device 100 has a general oblong or pebble shape and a replaceable mouthpiece 190 that extends from the main body of the aerosol-generating device 100. For example, the aerosol-generating device 100 may include a housing 120. The housing 120 may enclose a capsule connector 132, which may be mounted to a printed circuit board (PCB) within the housing 120. The capsule connector 132 defines a capsule-receiving cavity 130 (as shown in FIG. 1D). Additionally, the lid 110 is configured to open/close relative to the housing 120 and is coupleable to the replaceable mouthpiece 190. For example, the lid 110 may be fixedly coupled to the housing 120 at a first point 122 and releasably coupleable to the housing 120 at a second point 124. The first point 122 of the housing 120 may be on a first side 102 of the device 100. The second point 124 of the housing 120 may be on a second side 104 of the aerosol-generating device 100. In some instances, the lid 110 may also be referred to as a door. An exterior of the housing 120 and/or lid 110 may be formed from a metal (such as aluminum, stainless steel, and the like); an aesthetic, food contact rated plastic (such as, a polycarbonate (PC), acrylonitrile butadiene styrene (ABS) material, liquid crystalline polymer (LCP), a copolyester plastic, or any other suitable polymer and/or plastic); or any combination thereof. The replaceable mouthpiece 190 may be similarly formed from a metal (such as aluminum, stainless steel, and the like); an aesthetic, food contact rated plastic (such as, a polycarbonate (PC), acrylonitrile butadiene styrene (ABS) material, liquid crystalline polymer (LCP), a copolyester plastic, or any other suitable polymer and/or plastic); and/or plant-based materials (such as wood, bamboo, and the like). One or more interior surfaces or the housing 120 and/or lid 110 may be formed from or coated with a high temperature plastic (such as, polyetheretherketone (PEEK), liquid crystal polymer (LCP), or the like). The lid 110 and the housing 120 may be collectively regarded as the main body of the aerosol-generating device 100.

Figure 1B:
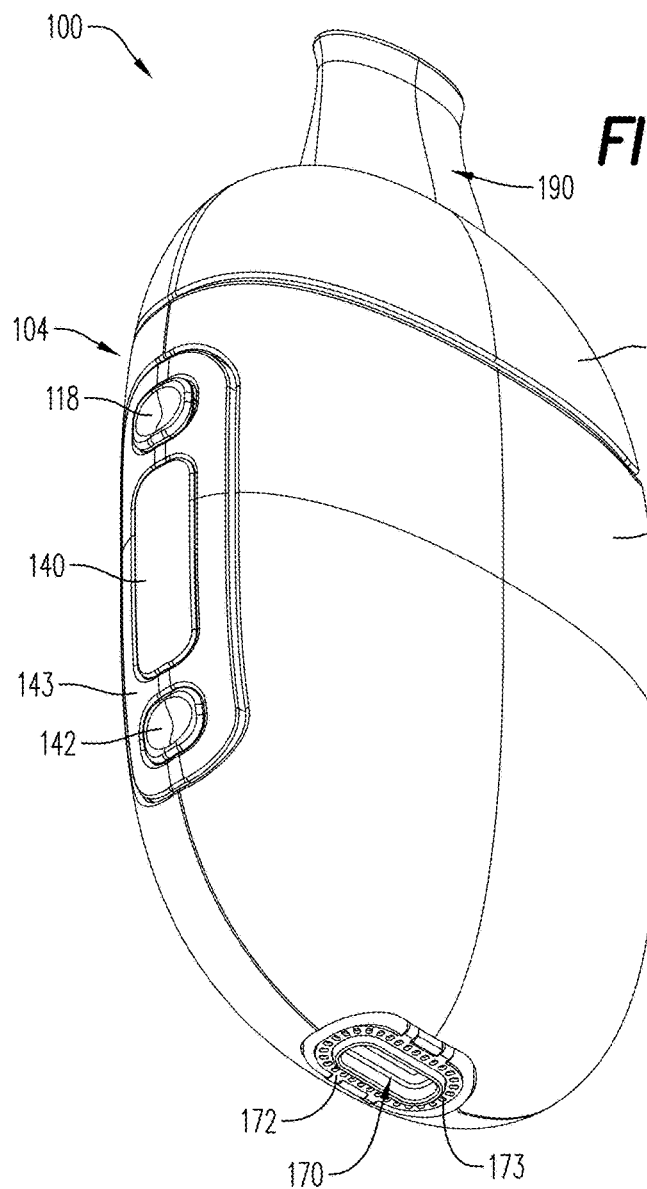
Figure 1C:
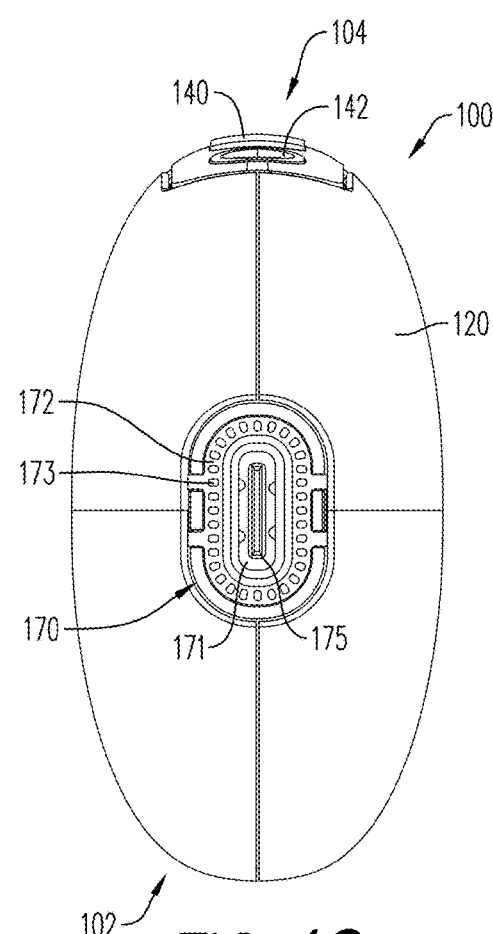
Figure 1D:
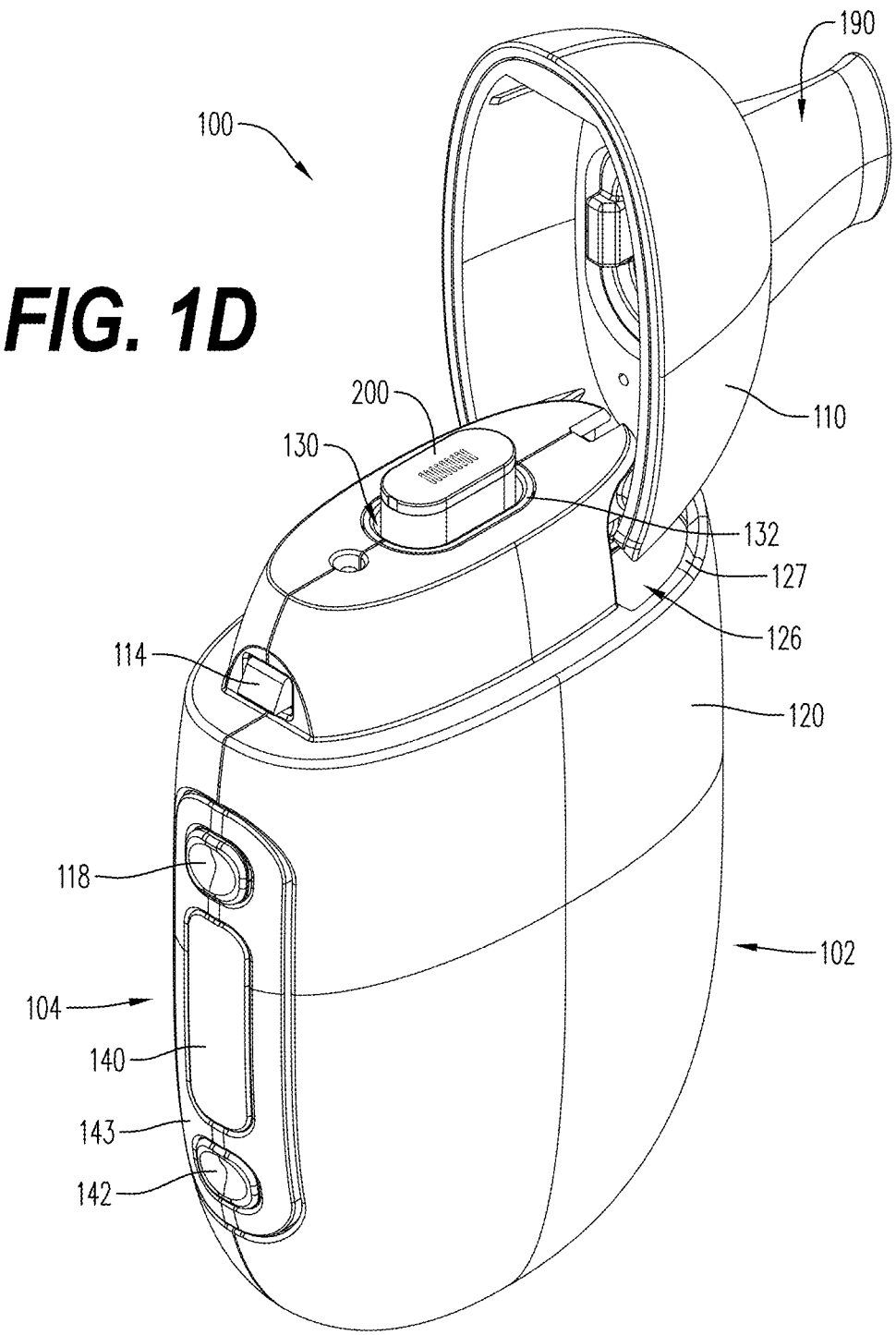

The lid 110 may be fixedly coupled to the housing 120 at the first point 122 by a hinge, or other similar connector, that allows the lid 110 to move (e.g., swing and rotate) from an open position (such as illustrated in FIG. 1D) to a closed position (such as illustrated in FIGS. 1A-1B). The hinge may include a torsion spring. In at least some example embodiments, such as illustrated in FIG. 1D, the housing 120 includes a recess 126 at the first point 122. The recess 126 may be configured to receive a portion of the lid 110 so as to allow for an easy and smooth movement of the lid 110 from the open position to the closed position (and vice versa). The recess 126 may have a structure that corresponds with a relative portion of the lid 110. For example, as illustrated, the recess 126 may include a substantially curved portion 127 that has a general concave shape that corresponds with the curvature of the lid 110, which has a general convex shape.

The lid 110 may be releasably coupleable to the housing 120 at the second point 124 by a latch 114, or other similar connector, that allows the lid 110 to be fixed or secured in the closed position and easily releasable so as to allow the lid 110 to move from the secured closed position to the open position. In at least one example embodiment, the latch 114 may be coupled to a latch release mechanism. The latch release mechanism may be configured to move the latch 114 from a first or closed position to a second or open position. For example, the latch 114 may extend downwards in the housing 120 and the latch release mechanism may be perpendicular to the downwards length of the latch 114. As such, the latch release mechanism is configured to apply pressure to the latch 114. For example, the latch release mechanism may be movable between a first position and a second position. In the first position, the latch release mechanism may be neutral relative to the latch 114. In the second position, the latch release mechanism may apply pressure to the downwards length of the latch 114 so as to move the latch 114 from the secured or latched close position to the open position.

In at least one example embodiment, the latch release mechanism is in communication with a latch release button 118 that is configured to activate the latch release mechanism—i.e., to move the latch 114 from the first or closed or secured position to the second or pressure-applying position and to move/return the latch 114 from the open position to the secured or closed position. In at least one example embodiment, the latch release button 118 is an adult consumer interaction button disposed on the second side 104 of the aerosol-generating device 100. For example, when the latch release button 118 is pressed by the adult consumer, the latch release mechanism may move from the first or closed or secured position to the second or pressure-applying position so as to move the latch 114 from the secured or closed position to the open position. The latch release button 118 may have a substantially circular shape with a center depression or dimple configured to direct the pressure applied by the adult consumer, although example embodiments are not limited thereto. One or more sensors (not shown) configured to detect the lid 110 opening and closure may be embedded or otherwise disposed within the housing 120 and/or one or more of the elements therein (e.g., latch 114, latch release mechanism, latch release button 118).

In at least some example embodiments, the housing 120 encases or houses the latch release mechanism, as well as a power source (e.g., power supply 2110 discussed below with regard to FIG. 3) and other electrical systems discussed in more detail later. The supply of current from the power source may be in response to a manual operation (e.g., button-activation) or an automatic operation (e.g., puff-activation).

In at least some example embodiments, such as best illustrated in FIGS. 1A-1B and 1D, the housing 120 includes a consumer interface panel 143 disposed on the second side 104 of the device 100. For example, the consumer interface panel 143 may be an oval-shaped panel that runs along the second side of the device 100. The consumer interface panel 143 may include the latch release button 118, such as discussed above, as well as a communication screen 140 and/or a power button 142. For example, in at least some example embodiments, the consumer interface panel 143 may include the communication screen 140 disposed between the latch release button 118 and the power button 142. As illustrated, the latch release button 118 may be disposed towards a top of the aerosol-generating device 100, and the power button 142 may be disposed towards bottom of the aerosol-generating device 100. Like the latch release button 118, the power button 142 may also be an adult consumer interaction button. The power button 142 may have a substantially circular shape with a center depression or dimple configured to direct the pressure applied by the adult consumer, although example embodiments are not limited thereto. The power button 142 may turn on and off the aerosol-generating device 100. Though only the two buttons are illustrated, it should be understood more or less buttons may be provided depending on the available features and desired adult consumer interface.

In at least one example embodiment, the communication screen 140 is an integrated thin-film transistor ("TFT") screen. In other example embodiments, the communication screen 140 may be a liquid crystal display (LCD), electronic paper (e-paper) display, an organic light emitting diode ("OLED"), light emitting diode ("LED") screen, or the like. The communication screen 140 is configured for adult consumer engagement and may have a generally oblong shape.

In at least some example embodiments, the housing 120 defines a charging connector or port 170. For example, as best illustrated in FIG. 1B, the charging connector 170 may be defined/disposed in a bottom end of the housing 120 distal from the capsule-receiving cavity 130. The charging connector 170 may be configured to receive an electric current (e.g., via a USB/mini-USB cable) from an external power source so as to charge the power source internal to the aerosol-generating device 100. For example, in at least one example embodiment, such as best illustrated in FIG. 1C, the charging connector 170 may be an assembly defining a cavity 171 that has a projection 175 within the cavity 171. In an example embodiment, the projection 175 does not extend beyond the rim of the cavity 171. In addition, the charging connector 170 may also be configured to send data to and/or receive data (e.g., via a USB/mini-USB cable) from another aerosol-generating device (e.g., heat-not-burn (HNB) aerosol-generating device) and/or other electronic device (e.g., phone, tablet, computer, and the like). In at least one embodiment, the aerosol-generating device 100 may instead or additionally be configured for wireless communication (e.g., via Bluetooth) with such other aerosol-generating devices and/or electronic devices.

In at least some example embodiments, such as best illustrated in FIG. 1C, a protective grille 172 is disposed around the charging connector 170. The protective grille 172 may be configured to help reduce or prevent debris ingress and/or the inadvertent blockage of the incoming airflow. For example, the protective grille 172 may define a plurality of pores 173 along its length or course. As illustrated, the protective grille 172 may have an annular form that surrounds the charging connector 170. In this regard, the pores 173 may also be arranged (e.g., in a serial arrangement) around the charging connector 170. Each of the pores 173 may have an oval or circular shape, although not limited thereto. In at least one example embodiment, the protective grille 172 may include an approved food contact material. For example, the protective grille 172 may include plastic, metal (e.g., stainless steel, aluminum), or a combination thereof. In at least some example embodiments, a surface of the protective grille 172 may be coated, for example with a thin layer of plastic, and/or anodized.

The pores 173 in the protective grille 172 may function as inlets for air drawn into the aerosol-generating device 100. During the operation of the aerosol-generating device 100, ambient air entering through the pores 173 in the protective grille 172 around the charging connector 170 will converge to form a combined flow that then travels to the capsule 200. For example, the pores 173 may be in fluidic communication with the capsule-receiving cavity 130. In at least some example embodiments, air may be drawn from the pores 173 and through the capsule-receiving cavity 130. For example, air may be drawn through a capsule 200 received by the capsule-receiving cavity 130 and out of the replaceable mouthpiece 190.

Additional details regarding the example embodiments shown in FIGS. 1A-1D are described in U.S. application Ser. No. 17/151,327, filed on Jan. 18, 2021, the entire contents of which are incorporated herein by reference.

The capsule 200, example embodiments of which will be discussed in more detail below, generally includes a housing defining inlet openings, outlet openings, and a chamber between the inlet openings and the outlet openings. An aerosol-forming substrate is disposed within the chamber of the housing. Additionally, a heater system may extend into the housing from an exterior thereof. The housing may include a body portion, an upstream portion and a downstream portion. The body portion of the housing includes a proximal end and a distal end. The upstream portion of the housing may be configured to engage with the distal end of the body portion. The downstream portion of the housing may be configured to engage with the proximal end of the body portion. As discussed in more detail below, the heater system may include a heater (also referred herein as a heater element or heating element) and a fuse element.

Figure 2A:
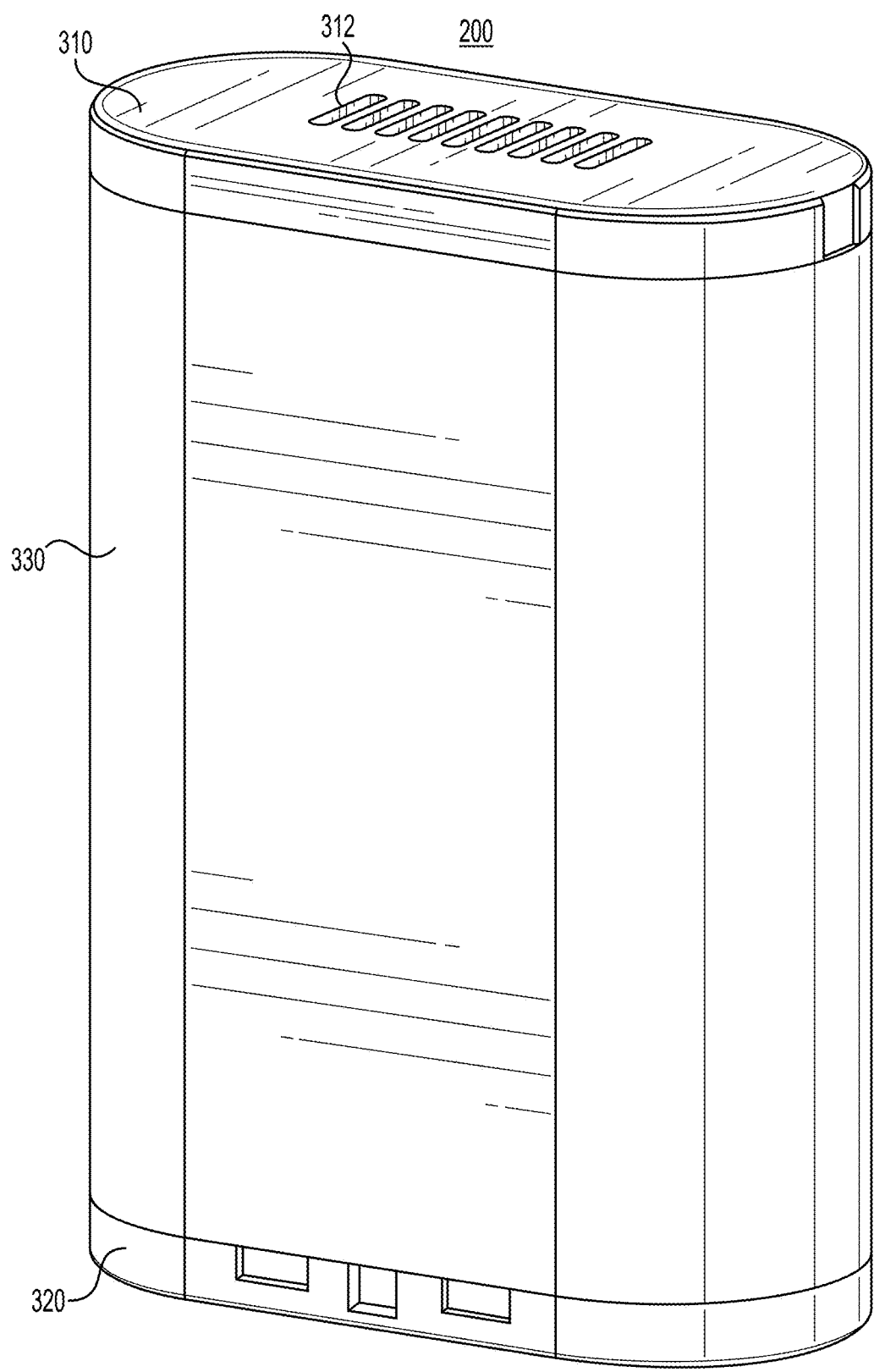
FIG. 2A is a perspective view of a capsule for an aerosol-generating device according to example embodiments.
Figure 2B:
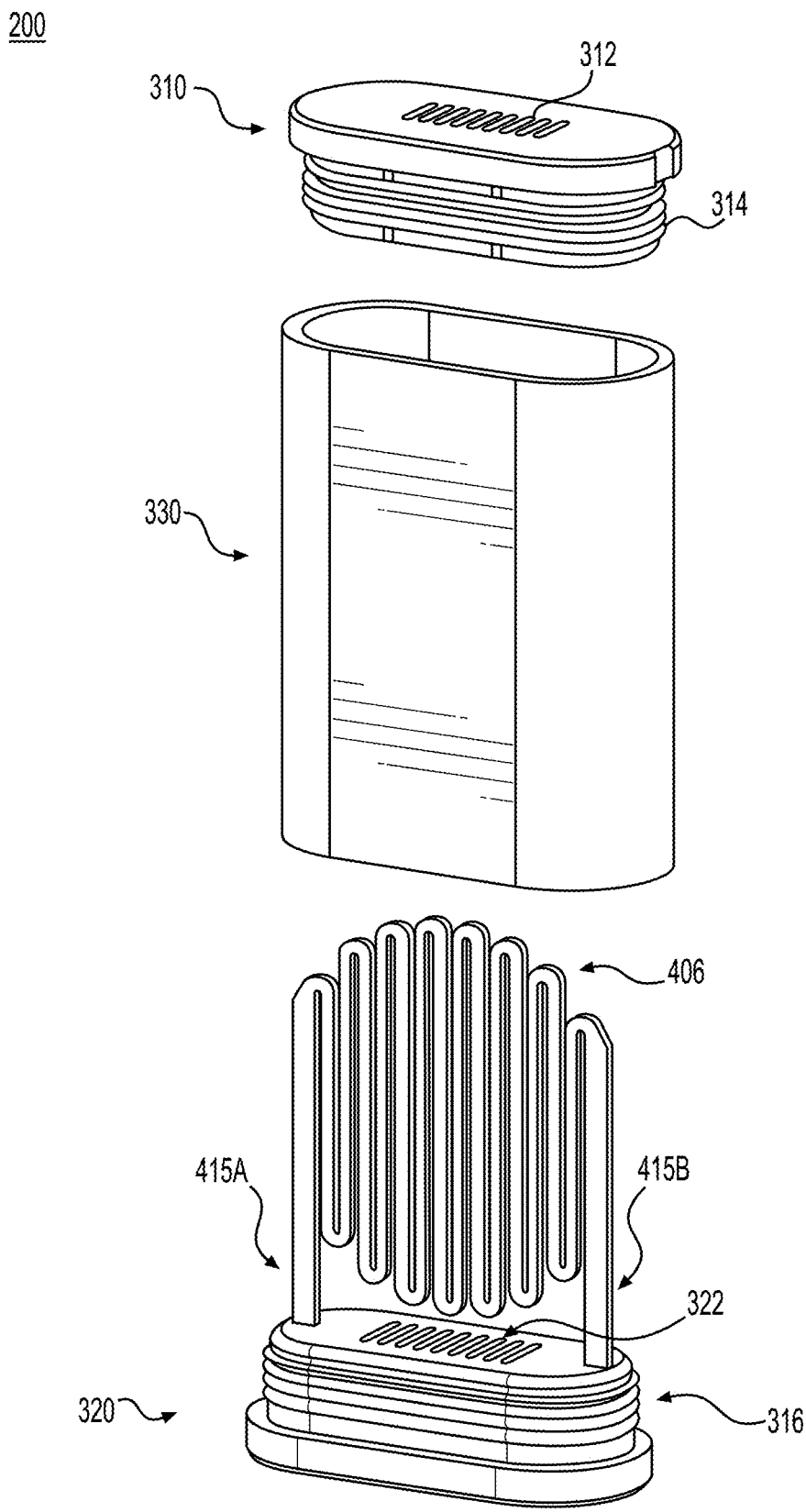
FIG. 2B is an exploded view of the capsule of FIG. 2A.
Figure 2C:
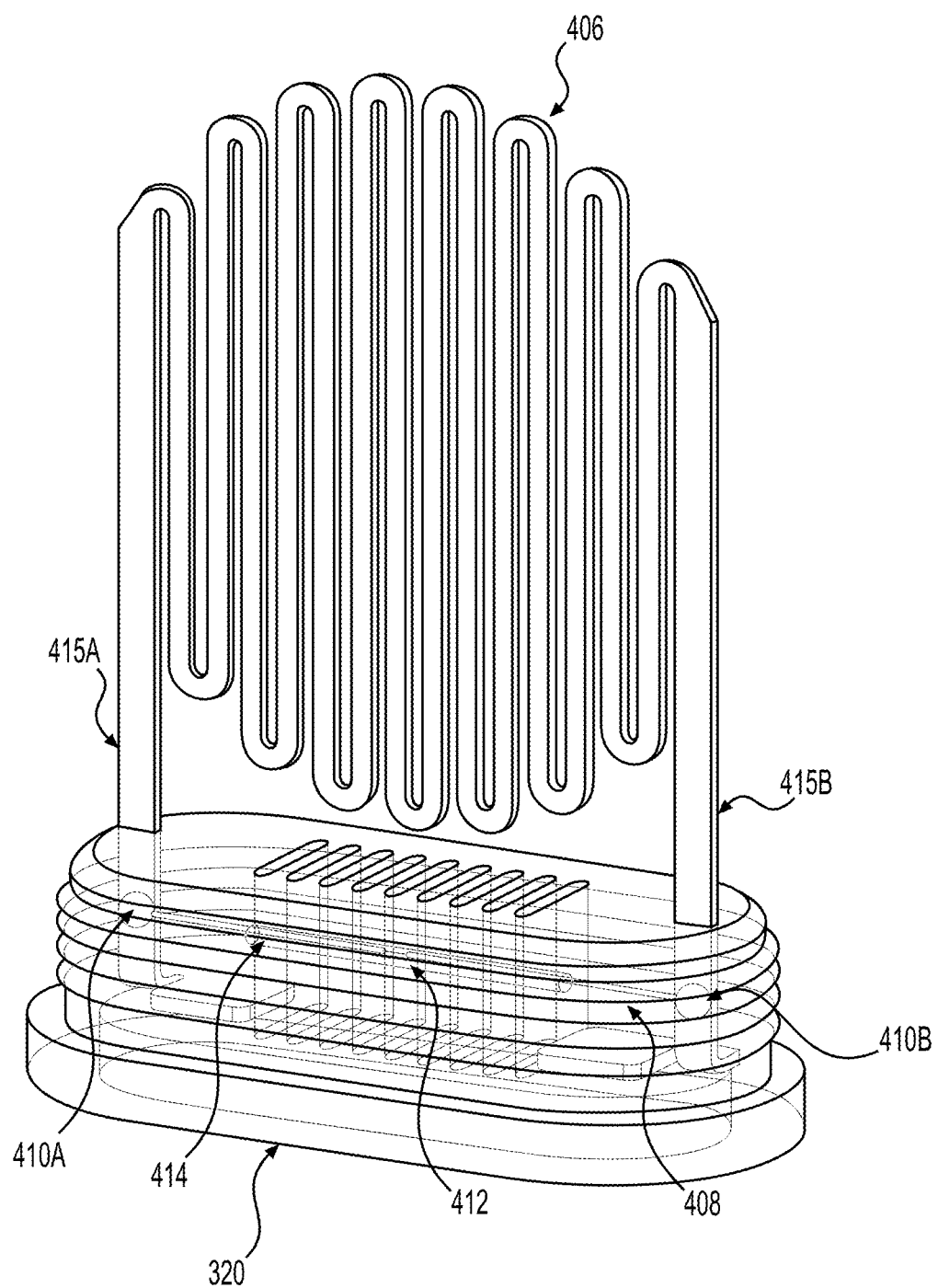
FIG. 2C illustrates the heater system and second end cap of FIG. 2B with the outer surface of the second end cap removed.
Figure 2D:
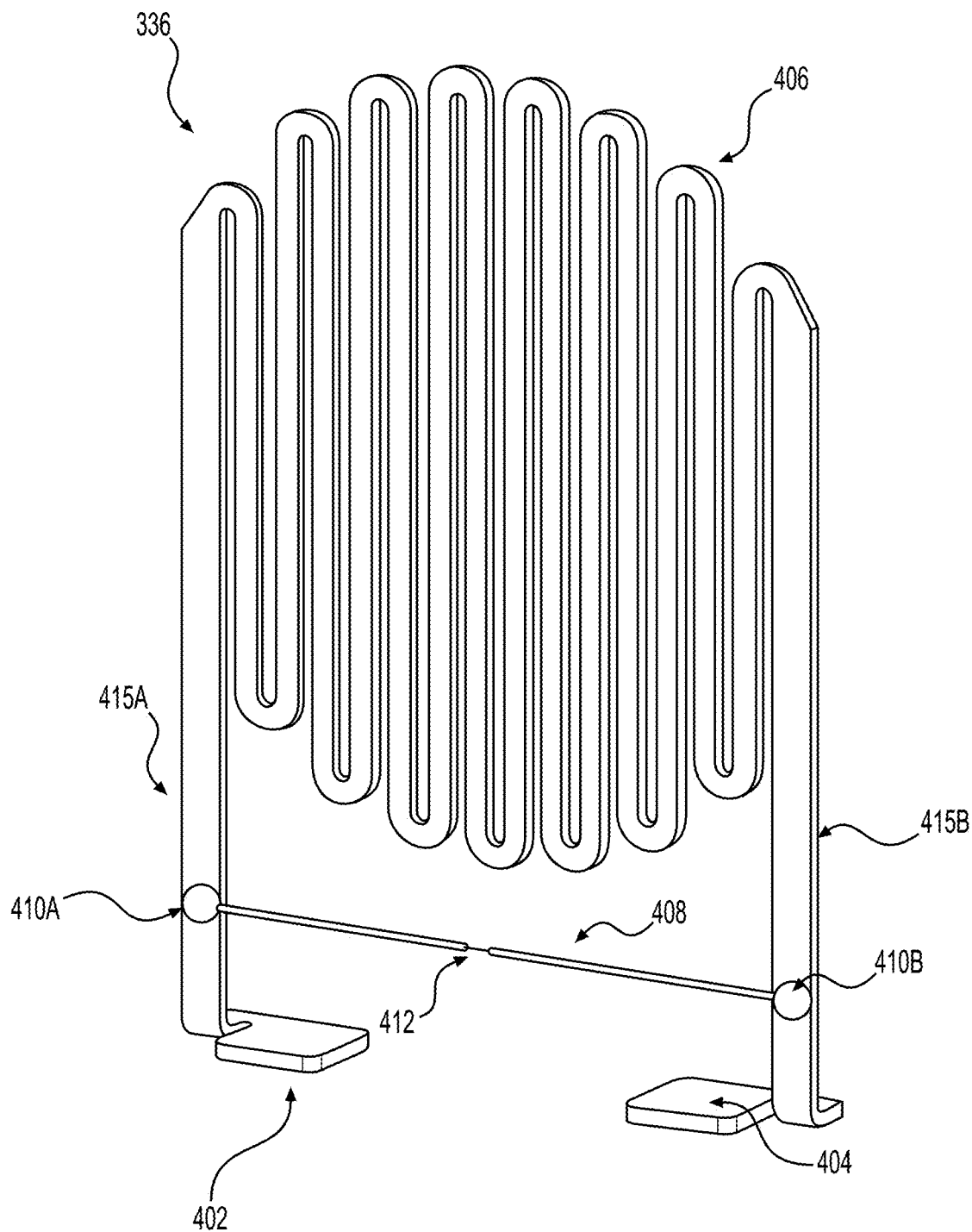
FIG. 2D is an enlarged view of the heater system shown in FIGS. 2B and 2C.

FIG. 2A is a perspective view of a capsule for an aerosol-generating device according to example embodiments. FIG. 2B is an exploded view of the capsule of FIG. 2A. FIG. 2C illustrates the heater system and second end cap of FIG. 2B with the outer surface of the second end cap removed. FIG. 2D is an enlarged view of the heater system partially shown in FIGS. 2B and 2C.

Referring to FIGS. 2A-2D, the capsule 200 includes a housing having a downstream portion, an upstream portion, and a body portion between the downstream portion and the upstream portion. The downstream portion of the housing may be in the form of a first end cap 310 (e.g., downstream cap). The upstream portion of the housing may be in the form of a second end cap 320 (e.g., upstream cap). The body portion of the housing may be in the form of a cover 330 (e.g., sleeve).

The capsule 200 further includes a heater system 36 arranged within the housing. In the example embodiment shown in FIGS. 2A-2D, the second end cap 320 is molded around an upstream portion of the heater system 36. According to one or more example embodiments, the heater system 36 may include, among other things, a heater 336 and a fuse element 408.

The second end cap 320, the heater system 36, and the engagement between the heater system 36 and the second end cap 320 will be discussed in more detail later.

The first end cap 310 defines first openings 312, while the second end cap 320 defines second openings 322. The second openings 322 extend through the second end cap 320 such that air flows through the second end cap 320 to the heater system 36.

The first end cap 310 may have a plurality of ridges 314 configured to provide a secure engagement between the first end cap 310 and the cover 330 at the downstream end.

The second end cap 320 may have a similar plurality of ridges 316 configured to provide a secure engagement between the second end cap 320 and the cover 330 at the upstream end.

The first end cap 310, the second end cap 320 and the cover 330 may be formed of molded plastic (e.g., liquid crystal polymer (LCP) plastic, or the like).

The heater 336 includes an intermediate section (heating section or region) 406 and terminals 402 and 404. Extension regions 415A and 415B electrically connect the heating region 406 to respective terminals 402 and 404. The fuse element (or fuse) 408 is electrically connected between the terminals 402 and 404 such that the fuse element 408 is electrically connected in parallel with the heater 336 (or resistance of the heater 336). In the example shown in FIG. 2D, ends of the fuse element 408 are spot welded to respective ones of the extension regions 415A and 415B.

The terminals 402 and 404 are configured to receive power (e.g., an electric current) from a power source (e.g., power supply 2110 in FIG. 3) via a heating engine control circuit (discussed later) to apply power to the heater system 36 (e.g., during preheating, activation of the heater to heat the aerosol-forming substrate, and/or during one or more methods discussed herein).

In the example embodiment shown in FIGS. 2A-2D, the heating region 406 has a planar and winding form resembling a compressed oscillation or zigzag with a plurality of parallel segments (e.g., eight to twelve parallel segments). However, it should be understood that other forms for the heating region 406 of the heater 336 are also possible (e.g., spiral form, flower-like form, or the like).

The fuse element 408 may be a one-time non-resettable fuse, in the form of a wire. The fuse element 408 may have a region 412 configured to induce a localized 'hot spot' to cause the fuse element 408 to open circuit (blow) in response to flow of current across the fuse element 408. According to at least one example embodiment, the region 412 may be a 'pinched' region (also referred to as a 'necked' region) of the fuse element 408. The fuse element 408 may be configured to have a resistance enabling a heating power required to activate the fuse element 408 to pass through the heater system 36.

In one example, if the nominal resistance $R_{NOMINAL}$ of the heater 336 is 2Ω, 10 W of heating power is applied to the heater 336, and 5 W of heating power is required to activate the fuse element 408, then the resistance of the fuse element 408 may be set to 2Ω. The majority of this resistance may be concentrated in the necked region in order to concentrate heating effects in the localized hot spot (superheating the metal to its vaporization point), thereby resulting in open-circuiting of the fuse element 408 when power is applied to the heater system 36.

In this example configuration, the initial resistance of the heater system (including the heater 336 and the fuse element 408) is 1Ω (two 2Ω resistors connected in parallel). When power is applied to the heater system 36, the resistance of the heater system 36 increases as the pinched region heats up until the fuse element 408 is open-circuited and the resistance of the heater system 36 (between the terminals 402 and 404) becomes equal or substantially equal to the nominal resistance $R_{NOMINAL}$ of the heater 336 with a relatively small delta (correction) for heating effects of the SW power passing through the heater 336.

In the example embodiment shown in FIGS. 2B-2D, the fuse element 408 may be ultrasonically, electrically or laser spot welded to respective extension regions leading to each of the terminals 402 and 404, for example at locations 410A and 410B on the extension regions 415A and 415B, respectively. In another example embodiment, the fuse element 408 may be formed integrally with the heater 336.

In a more detailed example, the fuse element 408 may be a filament wire, which may be ultrasonically welded to the respective extension regions 415A and 415B. This fuse element 408 may then be pinched or necked at or around the midpoint of the length to create a local area of relatively high resistance that becomes superheated when power is applied across the terminals 402 and 404. The superheating vaporizes the pinched area and causes the fuse element 408 to open circuit.

A sheet material may be cut or otherwise processed (e.g., stamping, electrochemical etching, die cutting, laser cutting, or the like) to produce the heater system 36 including the heater 336 (and the fuse element 408 if formed integrally with the heater 336). The sheet material may be formed of one or more conductors configured to undergo Joule heating (which is also known as ohmic/resistive heating). Suitable conductors for the sheet material include an iron-based alloy (e.g., stainless steel, iron aluminides), a nickel-based alloy (e.g., nichrome), and/or a ceramic (e.g., ceramic coated with metal). For instance, the stainless steel may be a type known in the art as SS316L, although example embodiments are not limited thereto. The sheet material may have a thickness of about 0.1-0.3 mm (e.g., 0.15-0.25 mm).

In this example, the fuse element 408 may be formed at the same or substantially the same time as the heater 336, and may have the same or substantially the same thickness as the heater 336.

After forming the fuse element 408, a post processing operation to pinch or 'neck' this larger structure may then be used to create a pinched or necked area 412 in the fuse element 408.

Although example embodiments are described herein with regard to the heater structure shown in FIGS. 2B-2D, example embodiments should not be limited to this example. Other heater structures such as those disclosed in U.S. application Ser. No. 17/151,327 may be utilized or combined with example embodiments discussed herein.

Still referring to FIGS. 2A-2D, the fuse element 408 may be enclosed in an area of the second end cap 320 where the air flow and the generated aerosol does not flow across or contact at least the necked area 412 of the fuse element 408.

In at least one example embodiment, the second end cap 320 may be over-molded on the pinched or 'necked' area of the fuse element 408 using plastic (e.g., liquid crystal polymer (LCP) plastic).

In one example, the second end cap 320 may be molded to enclose the fuse element 408 while also isolating the fuse element 408 from the air flow and aerosol flow path through the aerosol-generating device. The fuse element 408 may be isolated using a compartment or chamber 414 in the second end cap 320. In one example, the chamber 414 may have a length greater than or equal to the span of the length of the plurality of second openings 322.

In at least one example embodiment, the second end cap 320 includes the chamber 414 in the molding, and the fuse element 408 may be attached after the molding is complete.

In another example, if the fuse element 408 is integral with the heater 336, the chamber 414 may be formed by molding the second end cap 320 around the fuse element 408. In this example, the molding parameters may be set such that the molding pressures do not induce mechanical fracture of the fuse element 408. The fuse element 408 may be verified using, for example, x-ray inspection or direct measurement of the resistance of the heater system 36 after formation.

FIG. 3 illustrates electrical systems of an aerosol-generating device and a capsule according to at least some example embodiments.

Referring to FIG. 3, the electrical systems include an aerosol-generating device electrical system 2100 and a capsule electrical system 2200. The aerosol-generating device electrical system 2100 may be included in the aerosol-generating device 100, and the capsule electrical system 2200 may be included in the capsule 200.

In the example embodiment shown in FIG. 3, the capsule electrical system 2200 includes the heater system 36. As discussed above, the heater system 36 includes the heater 336 and the fuse element 408. The heater system 36 may also be referred to as a heater structure.

The capsule electrical system 2200 may further include a body electrical/data interface (not shown) for transferring power and/or data between the aerosol-generating device 100 and the capsule 200.

The aerosol-generating device electrical system 2100 includes a controller 2105, a power supply 2110, measurement circuits 2125, a heating engine control circuit 2127, aerosol indicators 2135, on-product controls 2150 (e.g., buttons 118 and 142 shown in FIGS. 1A-1D), a memory 2130, a clock circuit 2128 and an airflow sensor 185. In some example embodiments, the controller 2105, the power supply 2110, measurement circuits 2125, the heating engine control circuit 2127, the memory 2130, and the clock circuit 2128 may be on the same PCB (e.g., a main PCB, which is not shown). The aerosol-generating device electrical system 2100 may further include a capsule electrical/data interface (not shown) for transferring power and/or data between the aerosol-generating device 100 and the capsule 200.

The power supply 2110 may be an internal power source to supply power to the aerosol-generating device 100 and the capsule 200. The supply of power from the power supply 2110 may be controlled by the controller 2105 through power control circuitry (not shown). The power control circuitry may include one or more switches or transistors to regulate power output from the power supply 2110. The power supply 2110 may include one or more batteries (e.g., rechargeable dual battery arrangement, lithium-ion battery, fuel cells, or the like).

The controller 2105 may be configured to control overall operation of the aerosol-generating device 10. According to at least some example embodiments, the controller 2105 may include processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

In the example embodiment shown in FIG. 3, the controller 2105 is illustrated as a microcontroller including: input/output (I/O) interfaces, such as general purpose input/outputs (GPIOs), inter-integrated circuit ($I^2C$) interfaces, serial peripheral interface bus (SPI) interfaces, or the like; a multichannel analog-to-digital converter (ADC); and a clock input terminal. However, example embodiments should not be limited to this example. In at least one example implementation, the controller 2105 may be a microprocessor.

Example embodiments of methods and algorithms may be described herein as being performed by the controller 2105. However, example embodiments should not be limited to these examples. Rather, according to one or more example embodiments, methods and algorithms may be described as being performed by aerosol-generating devices including at least one processor and a memory storing computer-executable instructions, wherein the at least one processor is configured to execute the computer-readable instructions to cause the aerosol-generating device to perform operations of the method or algorithm. Additionally, the processor, memory and example algorithms, encoded as computer program code, may serve as means for providing or causing performance of operations discussed herein.

In FIG. 3, the memory 2130 is illustrated as being external to the controller 2105. In some example embodiments, however, the memory 2130 may be on board the controller 2105.

The controller 2105 is communicatively coupled to the measurement circuits 2125, the heating engine control circuit 2127, aerosol indicators 2135, the memory 2130, the on-product controls 2150, the clock circuit 2128, the power supply 2110 and the airflow sensor 185.

The heating engine control circuit 2127 and the airflow sensor 185 are connected to the controller 2105 via GPIO (General Purpose Input/Output) pins. The memory 2130 is connected to the controller 2105 via a SPI (Serial Peripheral Interface) pin. The clock circuit 2128 is connected to a clock input pin of the controller 2105. The aerosol indicators 2135 are connected to the controller 2105 via an $I^2C$ (Inter-Integrated Circuit) interface pin and a SPI/GPIO pin. The device sensors 2125 are connected to the controller 2105 through respective pins of the multi-channel ADC.

The clock circuit 2128 may be a timing mechanism, such as an oscillator circuit, to enable the controller 2105 to track idle time, aerosol-generating (draw) length, a combination of idle time and aerosol-generating (draw) length, application of power to the heater during capsule authentication and/or identification, or the like, of the aerosol-generating device 100. The clock circuit 2128 may also include a dedicated external clock crystal configured to generate the system clock for the aerosol-generating device 100.

The memory 2130 may be a non-volatile memory storing operational parameters and computer readable instructions for the controller 2105 to perform the algorithms described herein. In one example, the memory 2130 may be an electrically erasable programmable read-only memory (EEPROM), such as a flash memory or the like.

Still referring to FIG. 3, the measurement circuits 2125 may include a plurality of sensor or measurement circuits configured to provide signals indicative of sensor or measurement information to the controller 2105. In the example shown in FIG. 3, the measurement circuits 2125 include a heater current measurement circuit (also referred to as a current measurement circuit) 21258, a heater voltage measurement circuit (also referred to as a voltage measurement circuit) 21252, and a compensation voltage measurement circuit 21250.

The heater voltage measurement circuit 21252 may be configured to output (e.g., voltage) signals indicative of the voltage across the heater system 36 between terminals 402 and 404. An example embodiment of the heater voltage measurement circuit 21252 will be discussed in more detail later with regard to FIG. 4.

The heater current measurement circuit 21258 may be configured to output (e.g., voltage) signals indicative of the current through the heater system 36 between terminals 402 and 404. An example embodiment of the heater current measurement circuit 21258 will be discussed in more detail later with regard to FIG. 5.

The compensation voltage measurement circuit 21250 may be configured to output (e.g., voltage) signals indicative of the resistance of electrical power interface (e.g., electrical connector) between the capsule 200 and the aerosol-generating device 100. In some example embodiments, the compensation voltage measurement circuit 21250 may provide compensation voltage measurement signals to the controller 2105. Example embodiments of the compensation voltage measurement circuit 21250 will be discussed in more detail later with regard to FIG. 6.

As discussed above, the compensation voltage measurement circuit 21250, the heater current measurement circuit 21258 and the heater voltage measurement circuit 21252 are connected to the controller 2105 via pins of the multi-channel ADC. To measure characteristics and/or parameters of the aerosol-generating device 100 and the capsule 200 (e.g., voltage, current, resistance, temperature, or the like, of the heater system 36), the multi-channel ADC at the controller 2105 may sample the output signals from the measurement circuits 2125 at a sampling rate appropriate for the given characteristic and/or parameter being measured by the respective measurement circuit.

The airflow sensor 185 measures airflow through the aerosol-generating device 100. In at least one example embodiment, the sensor 185 may be a microelectromechanical system (MEMS) flow or pressure sensor or another type of sensor configured to measure air flow such as a hot-wire anemometer. In an example embodiment, the output of the sensor 185 to the controller 2105 is an instantaneous measurement of flow (in mL/s or $cm^3/s$) via a digital interface or SPI. In other example embodiments, the sensor 185 may be a hot-wire anemometer, a digital MEMS sensor or other known sensor. The sensor 185 may be operated as a puff sensor by detecting a draw when the flow value is greater than or equal to 1 mL/s, and terminating a draw when the flow value subsequently drops to 0 mL/s. In an example embodiment, the sensor 185 may be a MEMS flow sensor based differential pressure sensor with the differential pressure (in Pascals) converted to an instantaneous flow reading (in mL/s) using a curve fitting calibration function or a Look Up Table (of flow values for each differential pressure reading). In another example embodiment, the sensor 185 may be a capacitive pressure drop sensor.

The heating engine control circuit 2127 is connected to the controller 2105 via a GPIO pin. The heating engine control circuit 2127 is configured to control (enable and/or disable) the heating engine of the aerosol-generating device 100 by controlling power to the heater system 36. The heating engine control circuit 2127 is also configured to control the heating engine to apply a defined power profile to the heater system 36 during a capsule authentication and/or identification process, which will be discussed in more detail later.

The heating engine control circuit 2127 may disable the heating engine based on control signaling from the controller 2105.

The controller 2105 may control the aerosol indicators 2135 to indicate statuses and/or operations of the aerosol-generating device 100 to an adult consumer. The aerosol indicators 2135 may be at least partially implemented via the communication screen 140. The aerosol indicators 2135 may also include a vibrator, speaker, or other feedback mechanisms, and may indicate a current state of an adult consumer-controlled aerosol generating parameter (e.g., aerosol volume).

Still referring to FIG. 3, the controller 2105 may control power to the heater system 36 to heat the aerosol-forming substrate in accordance with a heating profile (e.g., heating based on volume, temperature, flavor, or the like). The heating profile may be determined based on empirical data and may be stored in the memory 2130.

The controller 2105 may also control power to the heater system 36 according to one or more fusing profiles to perform a capsule authentication and/or identification process. Methods for capsule identification and/or authentication according to example embodiments will be discussed in more detail later.

Figure 4:
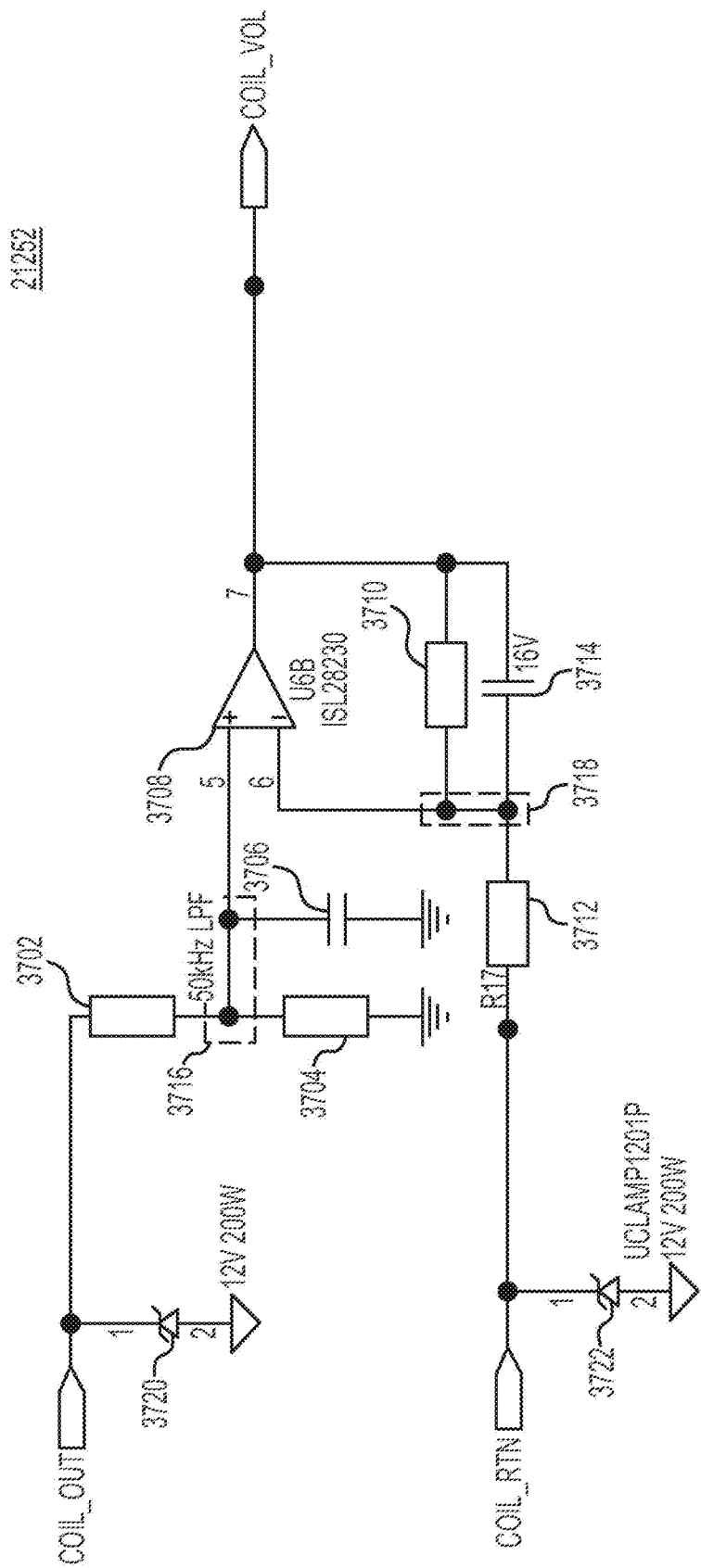
FIG. 4 illustrates a heater voltage measurement circuit according to example embodiments.

FIG. 4 illustrates an example embodiment of the heater voltage measurement circuit 21252.

Referring to FIG. 4, the heater voltage measurement circuit 21252 includes a resistor 3702 and a resistor 3704 connected in a voltage divider configuration between a terminal configured to receive an input voltage signal COIL_OUT and ground. The resistances of the resistor 3702 and the resistor 3704 may be 8.2 kiloohms and 3.3 kiloohms, respectively. The input voltage signal COIL_OUT is the voltage input to (voltage at the input terminal of) the heater system 36. A node N3716 between the resistor 3702 and the resistor 3704 is coupled to a positive input of an operational amplifier (Op-Amp) 3708. A capacitor 3706 is connected between the node N3716 and ground to form a low-pass filter circuit (an R/C filter) to stabilize the voltage input to the positive input of the Op-Amp 3708. The capacitance of the capacitor 3706 may be 18 nanofarads, for example. The filter circuit may also reduce inaccuracy due to switching noise induced by pulse width modulation (PWM) signals used to apply power and energize the heater system 36, and have the same phase response/group delay for both current and voltage.

The heater voltage measurement circuit 21252 further includes resistors 3710 and 3712 and a capacitor 3714. The resistor 3712 is connected between node N3718 and a terminal configured to receive an output voltage signal COIL_RTN and may have a resistance of 8.2 kiloohms, for example. The output voltage signal COIL_RTN is the voltage output from (voltage at the output terminal of) the heater system 36.

Resistor 3710 and capacitor 3714 are connected in parallel between node N3718 and an output of the Op-Amp 3708. The resistor 3710 may have a resistance of 3.3 kiloohms and the capacitor 3714 may have a capacitance of 18 nanofarads, for example. A negative input of the Op-Amp 3708 is also connected to node N3718. The resistors 3710 and 3712 and the capacitor 3714 are connected in a low-pass filter circuit configuration.

The heater voltage measurement circuit 21252 utilizes the Op-Amp 3708 to measure the voltage differential between the input voltage signal COIL_OUT and the output voltage signal COIL_RTN, and output a scaled heater voltage measurement signal COIL_VOL that represents the voltage across the heater system 36 between terminals 402 and 404. The heater voltage measurement circuit 21252 outputs the scaled heater voltage measurement signal COIL_VOL to an ADC pin of the controller 2105 for digital sampling and measurement by the controller 2105.

The gain of the Op-Amp 3708 may be set based on the surrounding passive electrical elements (e.g., resistors and capacitors) to improve the dynamic range of the voltage measurement. In one example, the dynamic range of the Op-Amp 3708 may be achieved by scaling the voltage so that the maximum voltage output matches the maximum input range of the ADC (e.g., about 2.5V). In at least one example embodiment, the scaling may be about 402 mV per V, and thus, the heater voltage measurement circuit 21252 may measure up to about 2.5V/0.402V=6.22V.

The voltage signals COIL_OUT and COIL_RTN are clamped by diodes 3720 and 3722, respectively, to reduce risk of damage due to electrostatic discharge (ESD) events.

In some example embodiments, four wire/Kelvin measurement may be used and the voltage signals COIL_OUT and COIL_RTN may be measured at measurement contact points (also referred to as voltage sensing connections (as opposed to main power contacts)) to take into account the contact and bulk resistances of an electrical power interface (e.g., electrical connector) between the heater system 36 and the aerosol-generating device 100.

Figure 5:
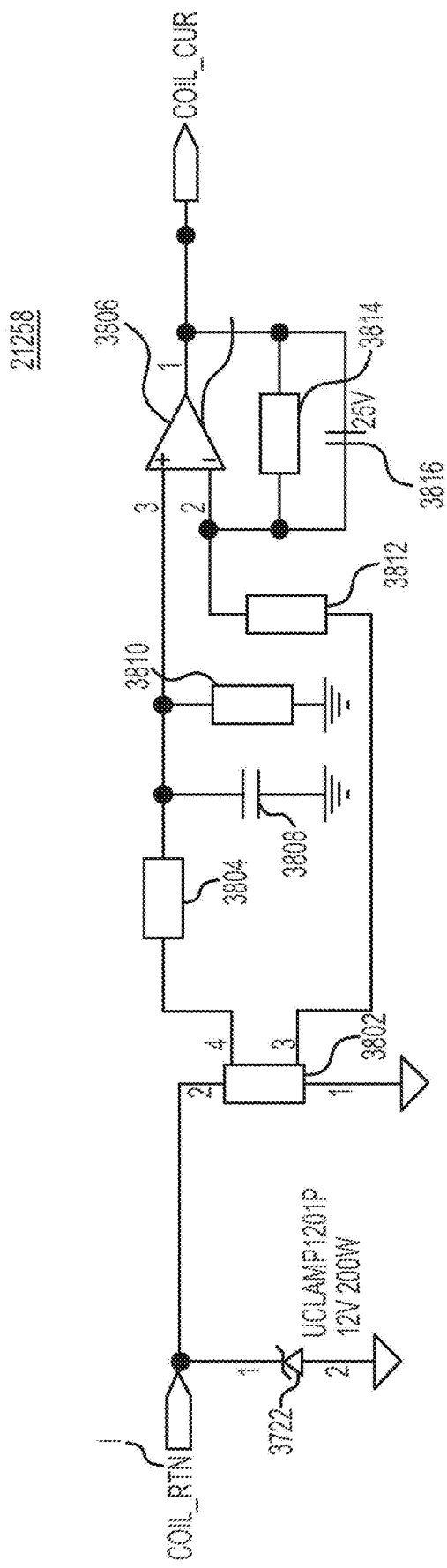
FIG. 5 illustrates a heater current measurement circuit according to example embodiments.

FIG. 5 illustrates an example embodiment of the heater current measurement circuit 21258 shown in FIG. 3.

Referring to FIG. 5, an output current signal COIL_RTN_I is input to a four terminal (4T) measurement resistor 3802 connected to ground. The differential voltage across the four terminal measurement resistor 3802 is scaled by an Op-Amp 3806, which outputs a heater current measurement signal COIL_CUR indicative of the current through the heater system 36. The heater current measurement signal COIL_CUR is output to an ADC pin of the controller 2105 for digital sampling and measurement of the current through the heater system 36 at the controller 2105.

In the example embodiment shown in FIG. 5, the four terminal measurement resistor 3802 may be used to reduce error in the current measurement using a four wire/Kelvin current measurement technique. In this example, separation of the current measurement path from the voltage measurement path may reduce noise on the voltage measurement path.

The gain of the Op-Amp 3806 may be set to improve the dynamic range of the measurement. In this example, the scaling of the Op-Amp 3806 may be about 0.820 V/A, and thus, the heater current measurement circuit 21258 may measure up to about 2.5 V/(0.820 V/A)=3.05 A.

Referring to FIG. 5 in more detail, a first terminal of the four terminal measurement resistor 3802 is connected to a terminal of the heater system 36 to receive the output current signal COIL_RTN_I. A second terminal of the four terminal measurement resistor 3802 is connected to ground. A third terminal of the four terminal measurement resistor 3802 is connected to a low-pass filter circuit (R/C filter) including resistor 3804, capacitor 3808 and resistor 3810. The resistance of the resistor 3804 may be 100 ohms, the resistance of the resistor 3810 may be 8.2 kiloohms and the capacitance of the capacitor 3808 may be 3.3 nanofarads, for example.

The output of the low-pass filter circuit is connected to a positive input of the Op-Amp 3806. The low-pass filter circuit may reduce inaccuracy due to switching noise induced by the PWM signals applied to energize the heater system 36, and may also have the same phase response/group delay for both current and voltage.

The heater current measurement circuit 21258 further includes resistors 3812 and 3814 and a capacitor 3816. The resistors 3812 and 3814 and the capacitor 3816 are connected to the fourth terminal of the four terminal measurement resistor 3802, a negative input of the Op-Amp 3806 and an output of the Op-Amp 3806 in a low-pass filter circuit configuration, wherein the output of the low-pass filter circuit is connected to the negative input of the Op-Amp 3806. The resistors 3812 and 3814 may have resistances of 100 ohms and 8.2 kiloohms, respectively, and the capacitor 3816 may have a capacitance of 3.3. nanofarads, for example.

The Op-Amp 3806 outputs a differential voltage as the heater current measurement signal COIL_CUR to an ADC pin of the controller 2105 for sampling and measurement of the current through the heater system 36 by the controller 2105.

According to at least this example embodiment, the configuration of the heater current measurement circuit 21258 is similar to the configuration of the heater voltage measurement circuit 21252, except that the low-pass filter circuit including resistors 3804 and 3810 and the capacitor 3808 is connected to a terminal of the four terminal measurement resistor 3802 and the low-pass filter circuit including the resistors 3812 and 3814 and the capacitor 3816 is connected to another terminal of the four terminal measurement resistor 3802.

The controller 2105 may average multiple samples (e.g., of voltage) over a time window (e.g., about 1 ms) corresponding to the 'tick' time (iteration time of a control loop) used in the aerosol-generating device 100, and convert the average to a mathematical representation of the voltage and current between terminals 402 and 404 (through the heater system 36) through application of a scaling value. The scaling value may be determined based on the gain settings implemented at the respective Op-Amps, which may be specific to the hardware of the aerosol-generating device 100.

The controller 2105 may filter the converted voltage and current measurements using, for example, a three tap moving average filter to attenuate measurement noise. The controller 2105 may then use the filtered measurements to calculate: resistance $R_{system}$ of the heater system ($R_{system}$=COIL_VOL/COIL_CUR), power $P_{system}$ applied to the heater system ($P_{system}$=COIL_VOL*COIL_CUR), or the like.

According to one or more example embodiments, the gain settings of the passive elements of the circuits shown in FIGS. 4 and/or 5 may be adjusted to match the output signal range to the input range of the controller 2105.

Figure 6:
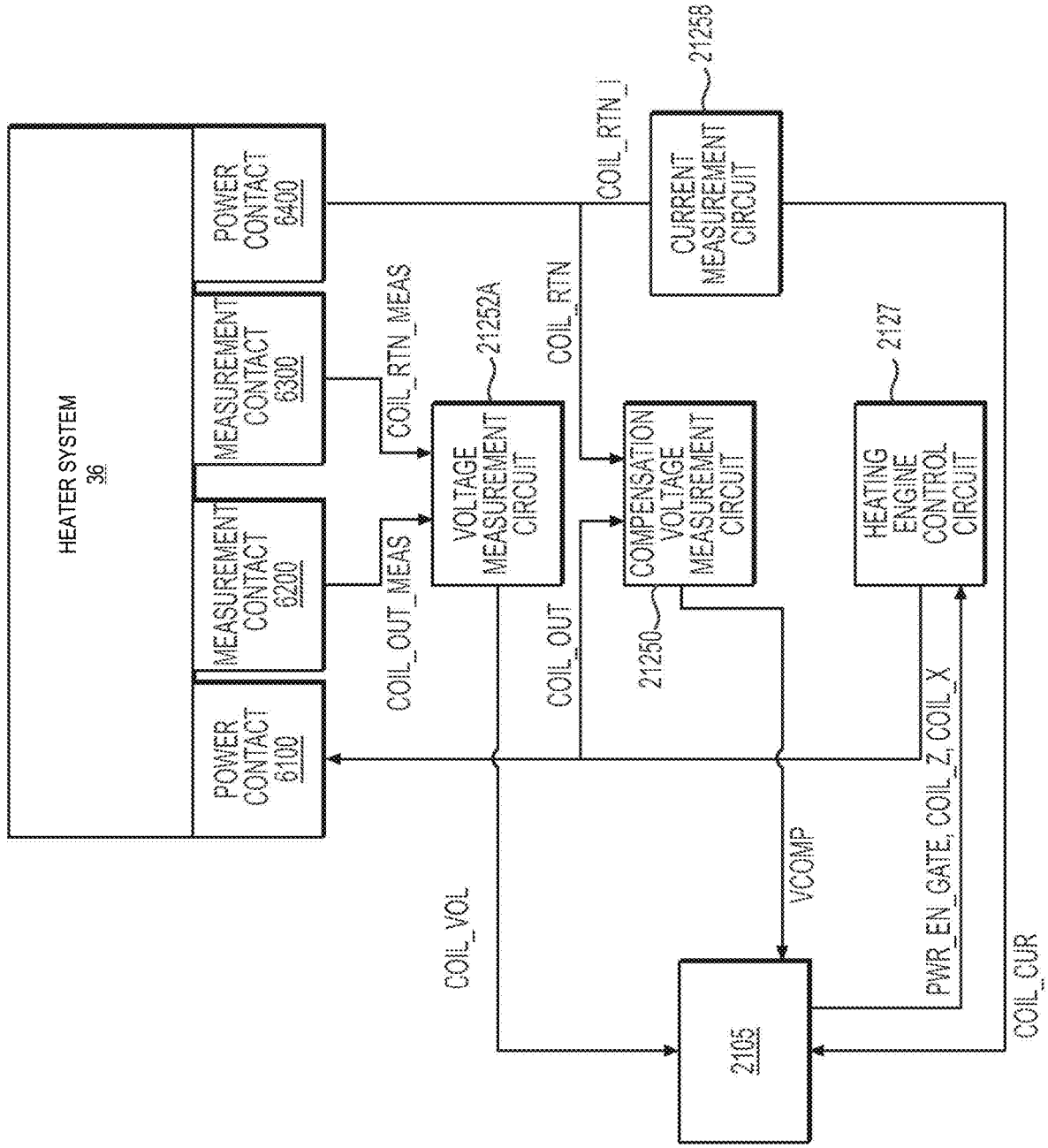
FIG. 6 illustrates a compensation voltage measurement circuit according to example embodiments.

FIG. 6 illustrates electrical systems of an aerosol-generating device including a separate compensation voltage measurement circuit according to one or more example embodiments.

As shown in FIG. 6, a contact interface between the heater system 36 and the aerosol-generating device electrical system 2100 includes a four wire/Kelvin arrangement having an input power contact 6100, an input measurement contact 6200, an output measurement contact 6300 and an output power contact 6400.

A voltage measurement circuit 21252A receives a measurement voltage COIL_OUT_MEAS at the input measurement contact 6200 and an output measurement voltage COIL_RTN_MEAS at the output measurement contact 6300. The heater voltage measurement circuit 21252A is the same circuit as the heater voltage measurement circuit 21252 illustrated in FIG. 4 and outputs the scaled heater voltage measurement signal COIL_VOL. While in FIG. 4 COIL_OUT and COIL_RTN are illustrated, it should be understood that in example embodiments without a separate compensation voltage measurement circuit, the heater voltage measurement circuit 21252 may receive voltages at the input and output measurement contacts 6200, 6300 instead of the input and output power contacts 6100, 6400.

The systems shown in FIG. 6 further include the compensation voltage measurement circuit 21250. The compensation voltage measurement circuit 21250 is the same as the heater voltage measurement circuit 21252A except the compensation voltage measurement circuit 21250 receives the voltage COIL_OUT at the input power contact 6100 and receives the voltage COIL_RTN at the output power contact 6400 and outputs a compensation voltage measurement signal VCOMP.

The heater current measurement circuit 21258 receives the output current signal COIL_RTN_I at the power contact 6400 and outputs the heater current measurement signal COIL_CUR.

Figure 7A:
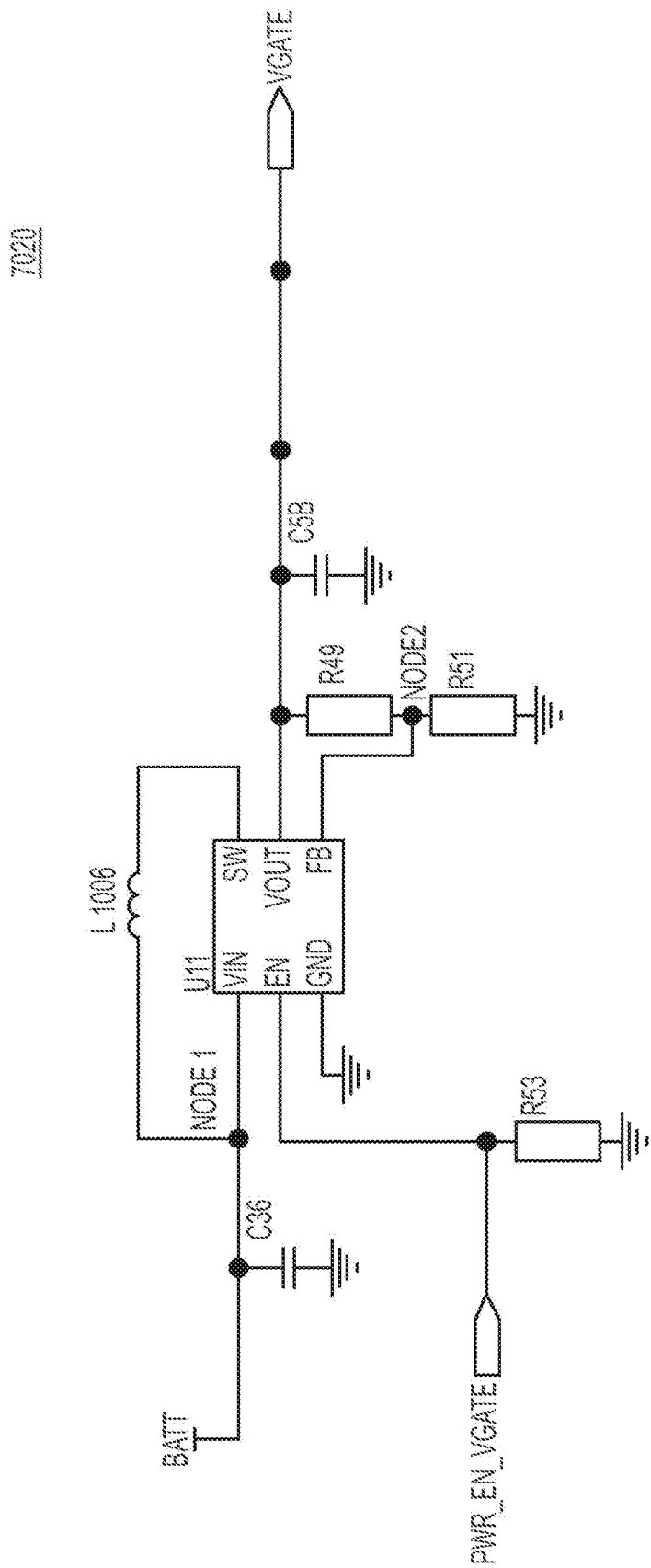
FIGS. 7A-7C illustrates a circuit diagrams illustrating a heating engine control circuit according to some example embodiments.
Figure 7B:
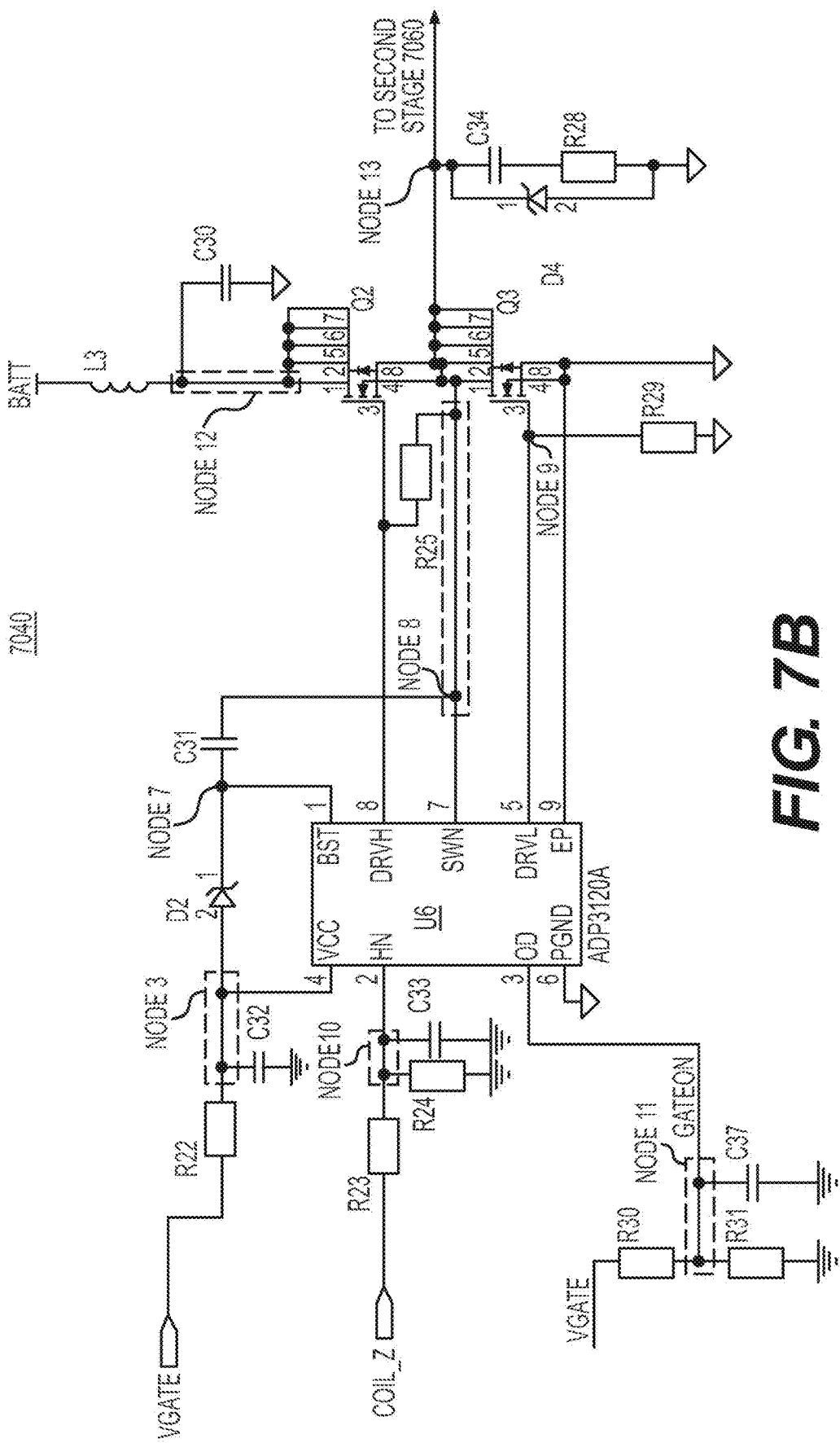
Figure 7C:
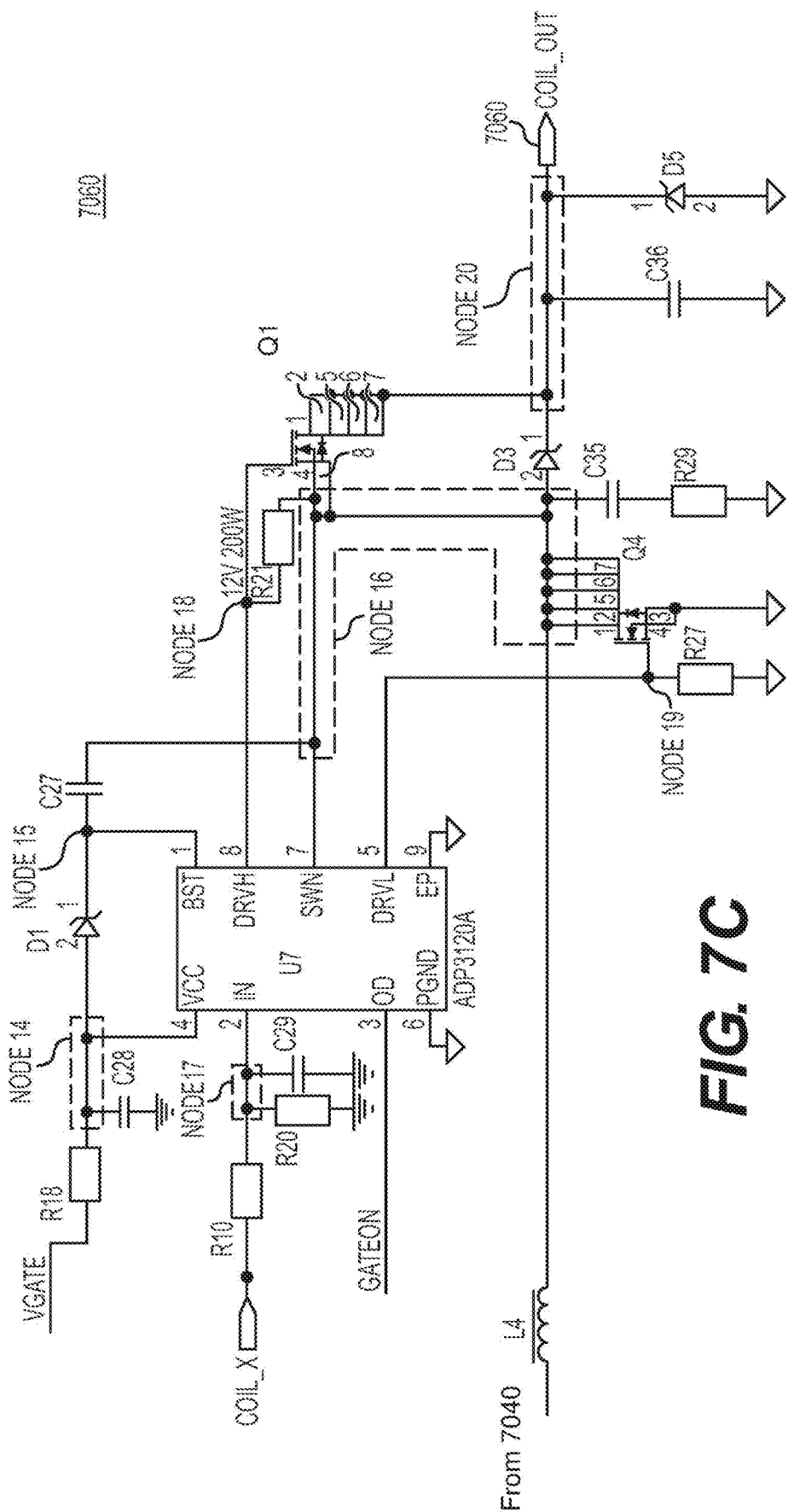

FIGS. 7A-7C is a circuit diagram illustrating a heating engine control circuit according to example embodiments. The heating engine control circuit shown in FIGS. 7A-7C is an example of the heating engine control circuit 2127 shown in FIG. 3.

The heating engine control circuit includes a boost converter circuit 7020 (FIG. 7A), a first stage 7040 (FIG. 7B) and a second stage 7060 (FIG. 7C).

The boost converter circuit 7020 is configured to create a voltage signal VGATE (e.g., 9V supply) (also referred to as a power signal or input voltage signal) from a voltage source BATT (e.g., power supply 2110 in FIG. 3) to power the first stage 7040 based on a first power enable signal PWR_EN_VGATE (also referred to as a shutdown signal). The controller 2105 may generate the first power enable signal PWR_EN_VGATE to have a logic high level when the aerosol-generating device 100 is ready to be used. In other words, the first power enable signal PWR_EN_VGATE has a logic high level when at least the controller 2105 detects that the capsule 200 is properly connected to the aerosol-generating device 100. In other example embodiments, the first power enable signal PWR_EN_VGATE has a logic high level when the controller 2105 detects that the capsule 200 is properly connected to the aerosol-generating device 100 and the controller 2105 detects an action such as a button being pressed.

The first stage 7040 utilizes the input voltage signal VGATE from the boost converter circuit 7020 to drive the heating engine control circuit 2127. The first stage 7040 and the second stage 7060 form a buck-boost converter circuit.

In the example embodiment shown in FIG. 7A, the boost converter circuit 7020 generates the input voltage signal VGATE only if the first enable signal PWR_EN_VGATE is asserted (present). The controller 2105 may disable VGATE to cut power to the first stage 7040 by de-asserting (stopping or terminating) the first enable signal PWR_EN_VGATE. The first enable signal PWR_EN_VGATE may serve as a device state power signal for performing an aerosol-generating-off operation at the aerosol-generating device 100. In this example, the controller 2105 may perform an aerosol-generating-off operation by de-asserting the first enable signal PWR_EN_VGATE, thereby disabling all power to the first stage 7040, the second stage 7060 and the heater 336. The controller 2105 may then enable aerosol-generating at the aerosol-generating device 100 by again asserting the first enable signal PWR_EN_VGATE to the boost converter circuit 7020.

The controller 2105 may generate the first enable signal PWR_EN_VGATE at a logic level such that boost converter circuit 7020 outputs the input voltage signal VGATE having a high level (at or approximately 9V) to enable power to the first stage 7040 and the heater system 36 in response to aerosol-generating conditions at the aerosol-generating device 100. The controller 2105 may generate the first enable signal PWR_EN_VGATE at another logic level such that boost converter circuit 7020 outputs the input voltage signal VGATE having a low level (at or approximately 0V) to disable power to the first stage 7040 and the heater system 36, thereby performing a heater-off operation.

Referring in more detail to the boost converter circuit 7020 in FIG. 7A, a capacitor C36 is connected between the voltage source BATT and ground. The capacitor C36 may have a capacitance of 10 microfarads.

A first terminal of inductor L1006 is connected to node Node1 between the voltage source BATT and the capacitor C36. The inductor L1006 serves as the main storage element of the boost converter circuit 7020. The inductor L1006 may have an inductance of 10 microhenrys.

Node Node 1 is connected to a voltage input pin VIN a boost converter chip U11. In some example embodiments, the boost converter chip may be a TPS61046YFFR.

A second terminal of the inductor L1006 is connected to a switch pin SW of the boost converter chip U11. An enable pin EN of the booster converter chip U11 is configured to receive the first enable signal PWR_EN_VGATE from the controller 2105.

In the example shown in FIG. 7A, the boost converter chip U11 serves as the main switching element of the boost converter circuit 7020.

A resistor R53 is connected between the enable pin EN of the booster converter chip U11 and ground to act as a pull-down resistor to ensure that operation of the heater system 36 is prevented when the first enable signal PWR_EN_GATE is in an indeterminate state. The resistor R53 may have a resistance of 100 kiloohms in some example embodiments.

A voltage output pin VOUT of the boost converter chip U11 is connected to a first terminal of a resistor R49 and first terminal of a capacitor C58. A second terminal of the capacitor C58 is connected to ground. A voltage output by the voltage output pin VOUT is the input voltage signal VGATE.

A second terminal of the resistor R49 and a first terminal of a resistor R51 are connected at a second node Node2. The second node Node2 is connected to a feedback pin FB of the booster converter chip U11. The boost converter chip U11 is configured to produce the input voltage signal VGATE at about 9V using the ratio of the resistance of the resistor R49 to the resistance of the resistor R51. In some example embodiments, the resistor R49 may have a resistance of 680 kiloohms and the resistor R51 may have a resistance of 66.5 kiloohms.

The capacitors C36 and C58 operate as smoothing capacitors and may have capacitances of 10 microfarads and 4.7 microfarads, respectively. The inductor L1006 may have an inductance selected based on a desired output voltage (e.g., 9V).

Referring now to FIG. 7B, the first stage 7040 receives the input voltage signal VGATE and a second enable signal COIL_Z. The second enable signal COIL_Z is a pulse-width-modulation (PWM) signal and is an input to the first stage 7040.

The first stage 7040 includes, among other things, an integrated gate driver U6 configured to convert low-current signal(s) from the controller 2105 to high-current signals for controlling switching of transistors of the first stage 7040. The integrated gate driver U6 is also configured to translate voltage levels from the controller 2105 to voltage levels required by the transistors of the first stage 7040. In the example embodiment shown in FIG. 7B, the integrated gate driver U6 is a half-bridge driver. However, example embodiments should not be limited to this example.

In more detail, the input voltage signal VGATE from the boost converter circuit 7020 is input to the first stage 7040 through a filter circuit including a resistor R22 and a capacitor C32. The resistor R22 may have a resistance of 10 ohms and the capacitor C32 may have a capacitance of 1 microfarad.

The filter circuit including the resistor R22 and the capacitor C32 is connected to the VCC pin (pin 4) of the integrated gate driver U6 and the anode of Zener diode D2 at node Node3. The second terminal of the capacitor C32 is connected to ground. The anode of the Zener diode D2 is connected to a first terminal of capacitor C32 and a boost pin BST (pin 1) of the integrated gate driver U6 at node Node7. A second terminal of the capacitor C31 is connected to the switching node pin SWN (pin 7) of the integrated gate driver U6 and between transistors Q2 and Q3 at node Node8. In the example embodiment shown in FIG. 7B, the Zener diode D2 and the capacitor C31 form part of a boot-strap charge-pump circuit connected between the input voltage pin VCC and the boost pin BST of the integrated gate driver U6. Because the capacitor C31 is connected to the input voltage signal VGATE from the boost converter circuit 7020, the capacitor C31 charges to a voltage almost equal to the input voltage signal VGATE through the diode D2. The capacitor C31 may have a capacitance of 220 nanofarads.

Still referring to FIG. 7B, a resistor R25 is connected between the high side gate driver pin DRVH (pin 8) and the switching node pin SWN (pin 7). A first terminal of a resistor R29 is connected to the low side gate driver pin DRVL at a node Node9. A second terminal of the resistor R29 is connected to ground.

A resistor R23 and a capacitor C33 form a filter circuit connected to the input pin IN (pin 2) of the integrated gate driver U6. The filter circuit is configured to remove high frequency noise from the second heater enable signal COIL_Z input to the input pin IN. The second heater enable signal COIL_Z is a PWM signal from the controller 2105. Thus, the filter circuit is designed to filter out high frequency components of a PWM square wave pulse train, slightly reduces the rise and fall times on the square wave edges so that transistors are turned on and off gradually.

A resistor R24 is connected to the filter circuit and the input pin IN at node Node10. The resistor R24 is used as a pull-down resistor, such that if the second heater enable signal COIL_Z is floating (or indeterminate), then the input pin IN of the integrated gate driver U6 is held at a logic low level to prevent activation of the heater system 36.

A resistor R30 and a capacitor C37 form a filter circuit connected to a pin OD (pin 3) of the integrated gate driver U6. The filter circuit is configured to remove high frequency noise from the input voltage signal VGATE input to the pin OD.

A resistor R31 is connected to the filter circuit and the pin OD at node Node11. The resistor R31 is used as a pull-down resistor, such that if the input voltage signal VGATE is floating (or indeterminate), then the pin OD of the integrated gate driver U6 is held at a logic low level to prevent activation of the heater system 36. The signal output by the filter circuit formed by the resistor R30 and the capacitor C37 is referred to as filtered signal GATEON. Resistors R30 and R31 are also a divider circuit such that the signal VGATE is divided down to ~2.5V for a transistor driver chip input.

The transistors Q2 and Q3 field-effect transistors (FETs) connected in series between the voltage source BATT and ground. In addition, a first terminal of an inductor L3 is connected to the voltage source BATT. A second terminal of the inductor L3 is connected to a first terminal of a capacitor C30 and to a drain of the transistor Q2 at a node Node12. A second terminal of the capacitor C30 is connected to ground. The inductor L3 and the capacitor C30 form a filter to reduce and/or prevent transient spikes from the voltage source BATT.

The gate of the transistor Q3 is connected to the low side gate driver pin DRVL (pin 5) of the integrated gate driver U6, the drain of the transistor Q3 is connected to the switching node pin SWN (pin 7) of the integrated gate driver U6 at node Node8, and the source of the transistor Q3 is connected to ground GND. When the low side gate drive signal output from the low side gate driver pin DRVL is high, the transistor Q3 is in a low impedance state (ON), thereby connecting the node Node8 to ground.

As mentioned above, because the capacitor C31 is connected to the input voltage signal VGATE from the boost converter circuit 7020, the capacitor C31 charges to a voltage equal or substantially equal to the input voltage signal VGATE through the diode D2.

When the low side gate drive signal output from the low side gate driver pin DRVL is low, the transistor Q3 switches to the high impedance state (OFF), and the high side gate driver pin DRVH (pin 8) is connected internally to the boost pin BST within the integrated gate driver U6. As a result, transistor Q2 is in a low impedance state (ON), thereby connecting the switching node SWN to the voltage source BATT to pull the switching node SWN (Node 8) to the voltage of the voltage source BATT.

In this case, the node Node7 is raised to a bootstrap voltage V(BST)≈V(VGATE)+V(BATT), which allows the gate-source voltage of the transistor Q2 to be the same or substantially the same as the voltage of the input voltage signal VGATE (e.g., V(VGATE)) regardless (or independent) of the voltage from the voltage source BATT. The circuit arrangement ensures that the BST voltage is not changed as the voltage of the voltage source drops, i.e., the transistors are efficiently switched even as the voltage of the voltage source BATT changes.

As a result, the switching node SWN (Node 8) provides a high current switched signal that may be used to generate a voltage output to the second stage 7060 (and a voltage output to the heater 336) that has a maximum value equal to the battery voltage source BATT, but is otherwise substantially independent of the voltage output from the battery voltage source BATT.

A first terminal of a capacitor C34 and an anode of a Zener diode D4 are connected to an output terminal to the second stage 7060 at a node Node13. The capacitor C34 and a resistor R28 are connected in series. A second terminal of the capacitor C34 and a first terminal of the resistor R28 are connected. A cathode of the Zener diode D4 and a second terminal of the resistor R28 are connected to ground.

The capacitor C34, the Zener diode D4 and the resistor R28 form a back EMF (electric and magnetic fields) prevention circuit that prevents energy from an inductor L4 (shown in FIG. 7C) from flowing back into the first stage 7040.

The resistor R25 is connected between the gate of the transistor Q2 and the drain of the transistor Q3. The resistor R25 serves as a pull-down resistor to ensure that the transistor Q2 switches to a high impedance more reliably.

The output of the first stage 7040 is substantially independent of the voltage of the voltage source and is less than or equal to the voltage of the voltage source. When the second heater enable signal COIL_Z is at 100% PWM, the transistor Q2 is always activated, and the output of the first stage 7040 is the voltage of the voltage source or substantially the voltage of the voltage source.

FIG. 7C illustrates the second stage 7060. The second stage 7060 boosts the voltage of the output signal from the first stage 7040. More specifically, when the second heater enable signal COIL_Z is at a constant logic high level, a third enable signal COIL_X may be activated to boost the output of the first stage 7040. The third enable signal COIL_X is a PWM signal from the controller 2105. The controller 2105 controls the widths of the pulses of the third enable signal COIL_X to boost the output of the first stage 7040 and generate the input voltage signal COIL_OUT. When the third enable signal COIL_X is at a constant low logic level, the output of the second stage 7060 is the output of the first stage 7040.

The second stage 7060 receives the input voltage signal VGATE, the third enable signal COIL_X and the filtered signal GATEON.

The second stage 7060 includes, among other things, an integrated gate driver U7 configured to convert low-current signal(s) from the controller 2105 to high-current signals for controlling switching of transistors of the second stage 7060. The integrated gate driver U7 is also configured to translate voltage levels from the controller 2105 to voltage levels required by the transistors of the second stage 7060. In the example embodiment shown in FIG. 7B, the integrated gate driver U7 is a half-bridge driver. However, example embodiments should not be limited to this example.

In more detail, the input voltage signal VGATE from the boost converter circuit 7020 is input to the second stage 7060 through a filter circuit including a resistor R18 and a capacitor C28. The resistor R18 may have a resistance of 10 ohms and the capacitor C28 may have a capacitance of 1 microfarad.

The filter circuit including the resistor R18 and the capacitor C28 is connected to the VCC pin (pin 4) of the integrated gate driver U7 and the anode of Zener diode D1 at node Node14. The second terminal of the capacitor C28 is connected to ground. The anode of the Zener diode D2 is connected to a first terminal of capacitor C27 and a boost pin BST (pin 1) of the integrated gate driver U7 at node Node15. A second terminal of the capacitor C27 is connected to the switching node pin SWN (pin 7) of the integrated gate driver U7 and between transistors Q1 and Q4 at node Node16.

In the example embodiment shown in FIG. 7C, the Zener diode D1 and the capacitor C27 form part of a boot-strap charge-pump circuit connected between the input voltage pin VCC and the boost pin BST of the integrated gate driver U7. Because the capacitor C27 is connected to the input voltage signal VGATE from the boost converter circuit 7020, the capacitor C27 charges to a voltage almost equal to the input voltage signal VGATE through the diode D1. The capacitor C31 may have a capacitance of 220 nanofarads.

Still referring to FIG. 7C, a resistor R21 is connected between the high side gate driver pin DRVH (pin 8) and the switching node pin SWN (pin 7). A gate of the transistor Q4 is connected to the low side gate driver pin DRVL (pin 5) of the integrated date driver U7.

A first terminal of the inductor L4 is connected to the output of the first stage 7040 and a second terminal of the inductor L4 is connected to the node Node16. The inductor L4 serves as the main storage element of the output of the first stage 7040. In example operation, when the integrated gate driver U7 outputs a low level signal from low side gate driver pin DRVL (pin 5), the transistor Q4 switches to a low impedance state (ON), thereby allowing current to flow through inductor L4 and transistor Q4. This stores energy in inductor L4, with the current increasing linearly over time. The current in the inductor is proportional to the switching frequency of the transistors (which is controlled by the third heater enable signal COIL_X).

A resistor R10 and a capacitor C29 form a filter circuit connected to the input pin IN (pin 2) of the integrated gate driver U7. The filter circuit is configured to remove high frequency noise from the third heater enable signal COIL_X input to the input pin IN.

A resistor R20 is connected to the filter circuit and the input pin IN at node Node17. The resistor R20 is used as a pull-down resistor, such that if the third heater enable signal COIL_X is floating (or indeterminate), then the input pin IN of the integrated gate driver U7 is held at a logic low level to prevent activation of the heater system 36.

A resistor R30 and a capacitor C37 form a filter circuit connected to a pin OD (pin 3) of the integrated gate driver U6. The filter circuit is configured to remove high frequency noise from the input voltage signal VGATE input to the pin OD.

The pin OD of the integrated gate driver U7 receives the filtered signal GATEON.

The transistors Q1 and Q4 field-effect transistors (FETs). A gate of the transistor Q1 and a first terminal of the resistor R21 are connected to the high side gate driver pin DRVH (pin 8) of the integrated gate driver U7 at a node Node18.

A source of the transistor Q1 is connected to a second terminal of the resistor R21, an anode of a Zener diode D3, a drain of the transistor Q4, a first terminal of a capacitor C35, a second terminal of the capacitor C27 and the switching node pin SWN (pin 7) of the integrated gate driver U7 at node Node16.

A gate of the transistor Q4 is connected to the low side gate driver pin DRVL (pin 5) of the integrated gate driver U7 and a first terminal of a resistor R27 at a node Node19. A source of the transistor Q4 and a second terminal of the resistor R27 are connected to ground.

A second terminal of the capacitor C35 is connected to a first terminal of a resistor R29. A second terminal of the resistor R29 is connected to ground.

A drain of the transistor Q1 is connected to a first terminal of a capacitor C36, a cathode of the Zener diode D3 and a cathode of a Zener diode D5 at a node Node20. A second terminal of the capacitor C36 and an anode of the Zener diode D5 are connected to ground. An output terminal 7065 of the second stage 7060 is connected to the node Node20 and outputs the input voltage signal COIL_OUT. The output terminal 7065 serves as the output of the heating engine control circuit 2127.

The capacitor C35 may be a smoothing capacitor and the resistor limits inrush current. The Zener diode D3 is a blocking diode to stop a voltage in the node Node20 discharging into the capacitor C35. The capacitor C36 is an output capacitor charged by the second stage 7060 (and reduces ripple in COIL_OUT) and the Zener diode D5 is an ESD (electrostatic discharge) protection diode.

When the low side gate drive signal output from the low side gate driver pin DRVL is high, the transistor Q4 is in a low impedance state (ON), thereby connecting the node Node16 to ground and increasing the energy stored in the magnetic field of the inductor L4.

As mentioned above, because the capacitor C27 is connected to the input voltage signal VGATE from the boost converter circuit 7020, the capacitor C27 charges to a voltage equal or substantially equal to the input voltage signal VGATE through the diode D1.

When the low side gate drive signal output from the low side gate driver pin DRVL is low, the transistor Q4 switches to the high impedance state (OFF), and the high side gate driver pin DRVH (pin 8) is connected internally to the bootstrap pin BST within the integrated gate driver U7. As a result, transistor Q1 is in a low impedance state (ON), thereby connecting the switching node SWN to the inductor L4.

In this case, the node Node 15 is raised to a bootstrap voltage $V(BST) \approx V(VGATE) + V(INDUCTOR)$, which allows the gate-source voltage of the transistor Q1 to be the same or substantially the same as the voltage of the input voltage signal VGATE (e.g., V(VGATE)) regardless (or independent) of the voltage from the inductor L4. As the second stage 7060 is a boost circuit, the bootstrap voltage may also be referred to as a boost voltage.

The switching node SWN (Node 8) is connected to the inductor voltage and the output capacitor C36 is charged, generating the voltage output signal COIL_OUT (the voltage output to the heater 336) that is substantially independent of the voltage output from the first stage 7040.

FIG. 8 illustrates a block diagram illustrating a temperature heating engine control algorithm according to at least some example embodiments.

Referring to FIG. 8, the temperature heating engine control algorithm 900 uses a proportional-integral-derivative (PID) controller 970 to control an amount of power applied to the heating engine control circuit 2127 so as to achieve a desired temperature. For example, as is discussed in greater detail below, according to at least some example embodiments, the temperature heating engine control algorithm 900 includes obtaining a determined temperature value 974 (e.g., determined as described above); obtaining a target temperature value (e.g., target temperature 976) from the memory 2130; and controlling, by a PID controller (e.g., PID controller 970), a level of power provided to the heater, based on the determined heater temperature value and the target temperature value.

Further, according to at least some example embodiments, the target temperature 976 serves as a setpoint (i.e., a temperature setpoint) in a PID control loop controlled by the PID controller 970.

Consequently, the PID controller 970 continuously corrects a level of the power control signal 972 so as to control a power waveform 930 (i.e., COIL_X and COIL_Z) output by the power level setting operation 944 to the heating engine control circuit 2127 in such a manner that a difference (e.g., a magnitude of the difference) between the target temperature 976 and the determined temperature 974 is reduced or, alternatively, minimized. The difference between the target temperature 976 and the determined temperature 974 may also be viewed as an error value which the PID controller 970 works to reduce or minimize.

For example, according to at least some example embodiments, the power level setting operation 944 outputs the power waveform 930 such that levels of the power waveform 930 are controlled by the power control signal 972. The heating engine control circuit 2127 causes an amount of power provided to the heater system 36 by the power supply 2110 to increase or decrease in manner that is proportional to an increase or decrease in a magnitude of the power levels of a power level waveform output to the heating engine control circuit 2127. Consequently, by controlling the power control signal 972, the PID controller 970 controls a level of power (or power profile) provided to the heater system 36 (e.g., by the power supply 2110) such that a magnitude of the difference between a target temperature value (e.g., target temperature 976) and a determined temperature value (e.g., determined temperature 974) is reduced, or alternatively, minimized.

Figure 11:
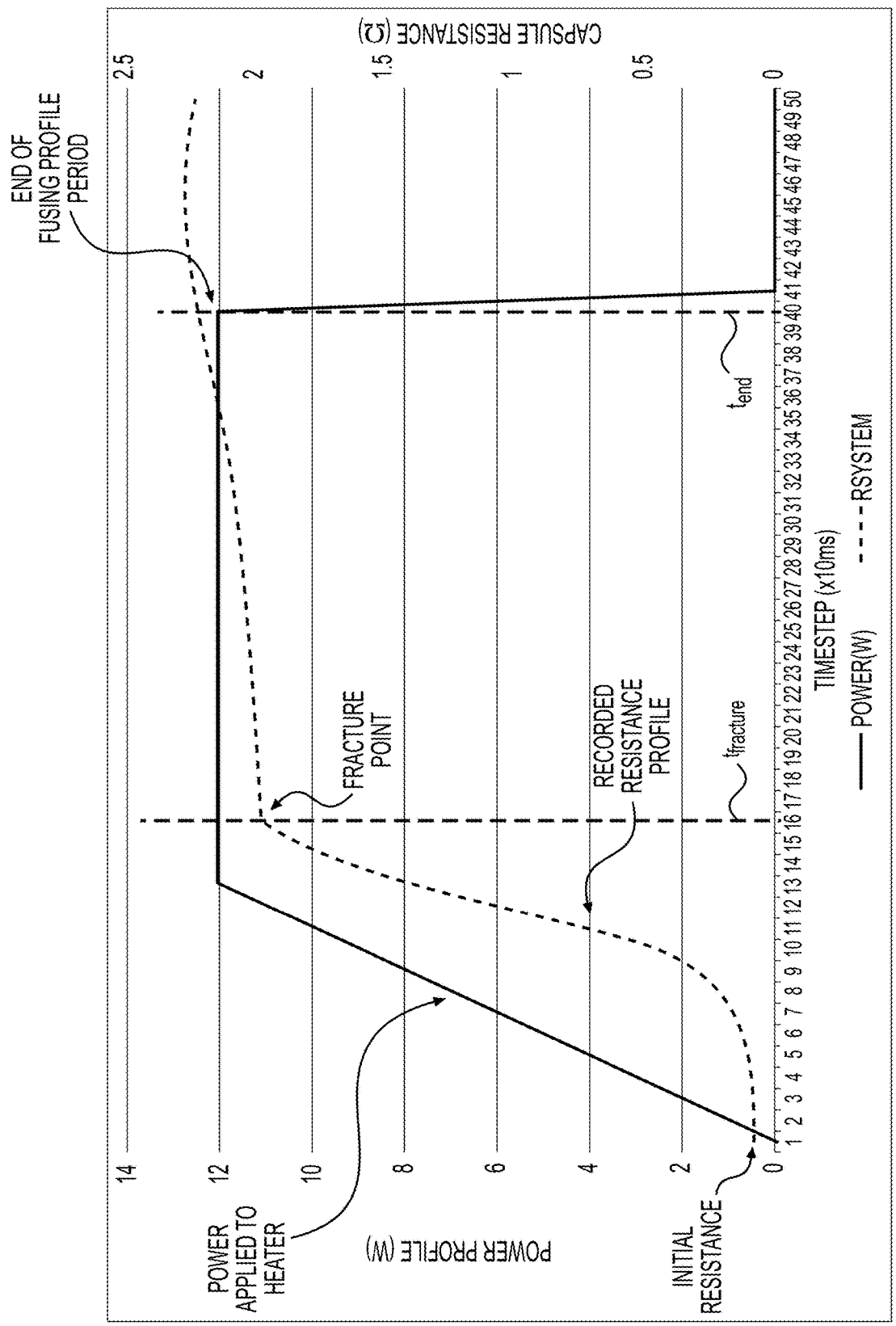
FIG. 11 is a graph illustrating an example power profile and corresponding recorded resistance profile according to at least some example embodiments.
Figure 12:
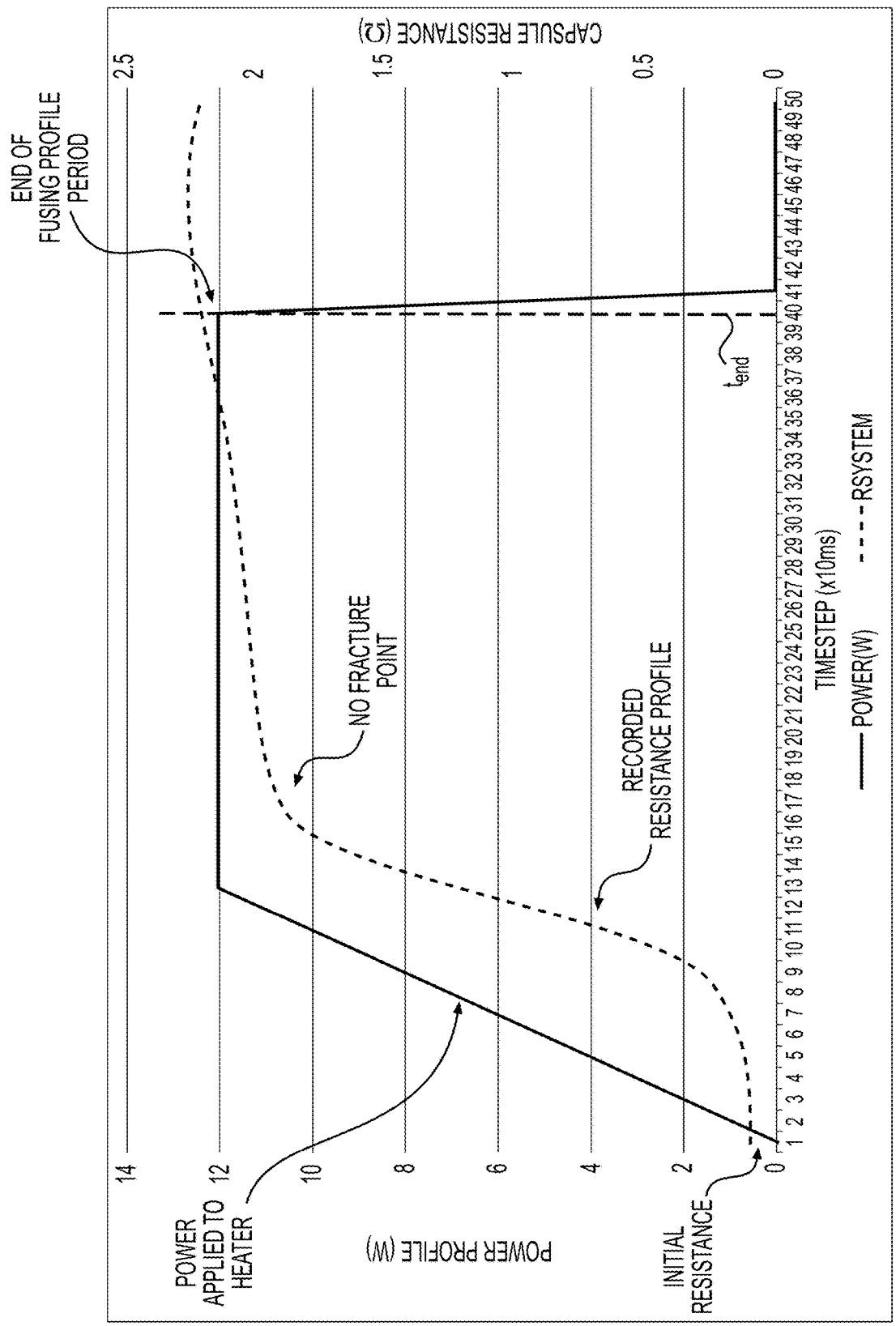
FIG. 12 is a graph illustrating another example power profile and corresponding recorded resistance profile according to at least some example embodiments.
Figure 13:
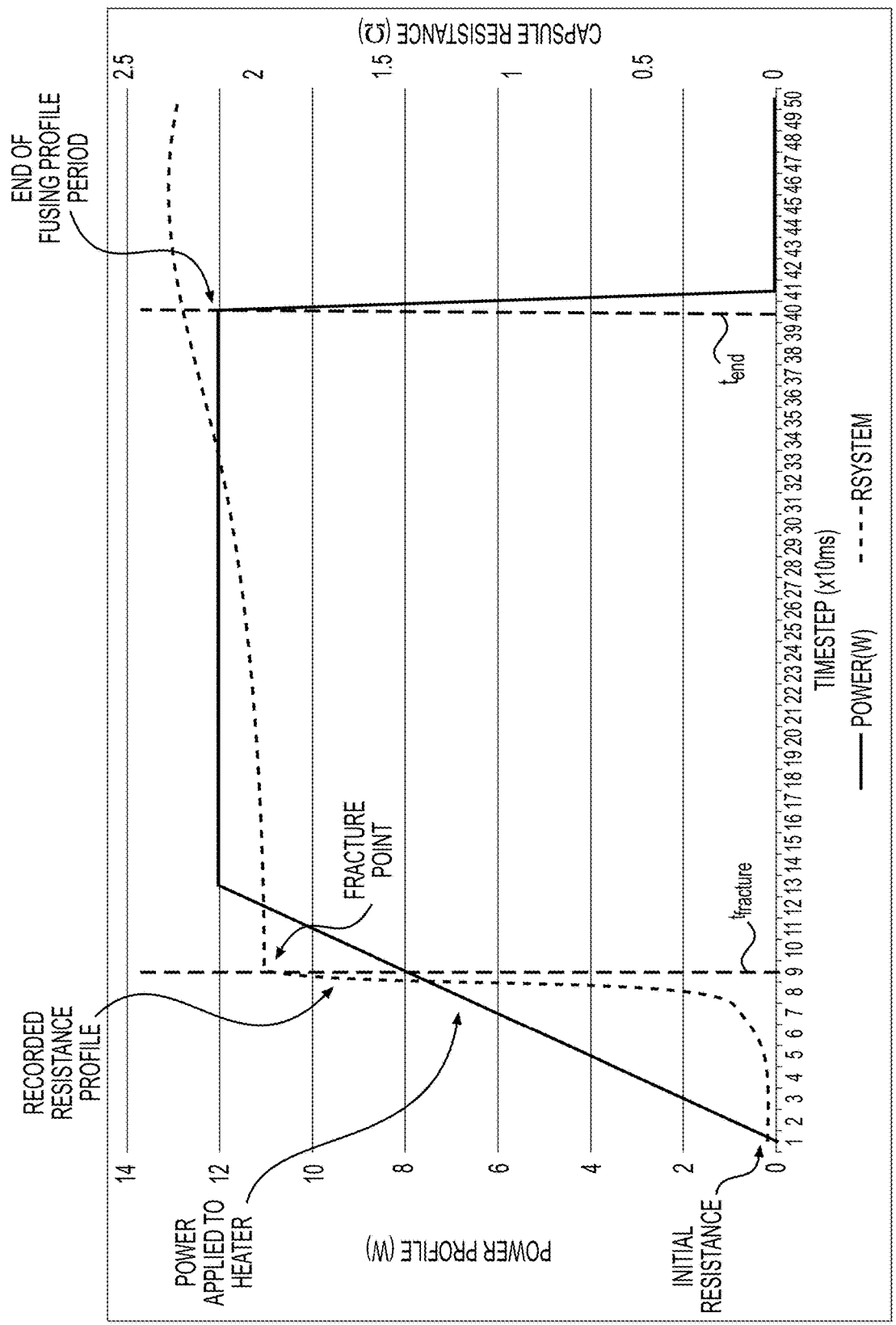
FIG. 13 is a graph illustrating yet another example power profile and corresponding recorded resistance profile according to at least some example embodiments.

According to at least some example embodiments, the PID controller 970 may operate in accordance with known PID control methods. According to at least some example embodiments, the PID controller 970 may generate 2 or more terms from among the proportional term (P), the integral term (I), and the derivative term (D), and the PID controller 970 may use the two or more terms to adjust or correct the power control signal 972 in accordance with known methods. Example power profiles are shown in FIGS. 11-13.

Additional details regarding the example embodiments shown in FIGS. 3-8 are described in U.S. application Ser. No. 17/151,375, filed on Jan. 18, 2021, the entire contents of which are incorporated herein by reference.

Figure 9:
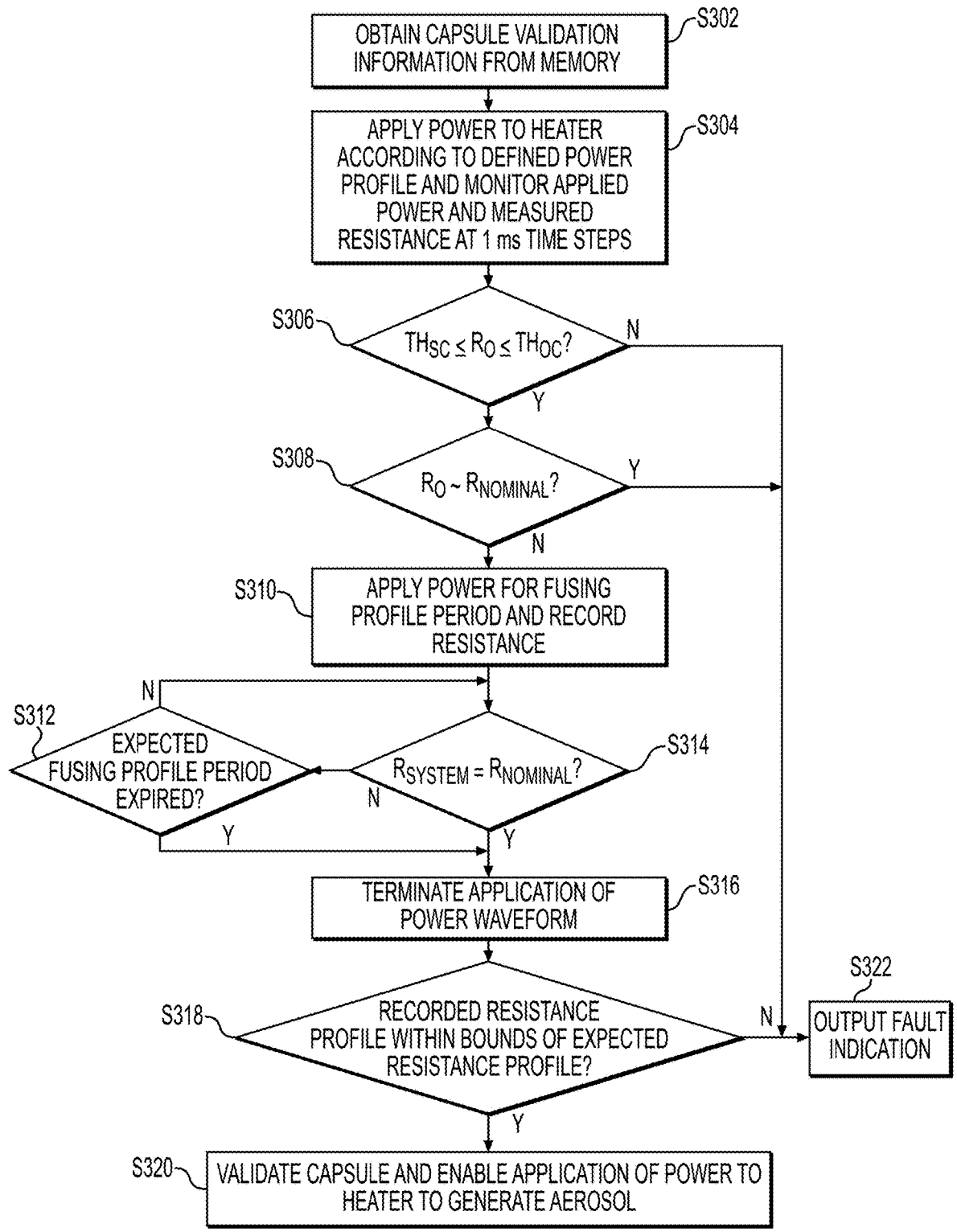
FIG. 9 is a flow chart illustrating a method of controlling an aerosol-generating device according to at least some example embodiments.

FIG. 9 is a flow chart illustrating a method for controlling an aerosol-generating device according to example embodiments. More specifically, FIG. 9 is a flow chart illustrating a method for validating a capsule of an aerosol-generating device according to example embodiments. For example purposes, the flow chart shown in FIG. 9 will be discussed with regard to the devices and electrical systems described herein. It should be understood, however, that example embodiments should not be limited to these examples. Rather, example embodiments may be applicable to other aerosol-generating devices and electrical systems thereof. Moreover, the example embodiment shown in FIG. 9 will be described with regard to operations performed by the controller 2105. However, example embodiments should not be limited to this example.

The example embodiment shown in FIG. 9 may be performed to detect and/or determine whether a capsule inserted into an aerosol-generating device is valid. As discussed herein, a valid capsule may refer to an authentic, properly manufactured capsule (e.g., a capsule of appropriate quality and within manufacturing tolerances), a capsule that has not been damaged or tampered with prior to insertion into an aerosol-generating device, a capsule that has not previously had power applied to the capsule so as to open circuit the fuse element (e.g., via previous insertion into and application of power by an aerosol-generating device to heat an aerosol-forming substrate in the capsule), or the like.

Referring to FIG. 9, when the capsule 200 is inserted into the aerosol-generating device 100, and the aerosol-generating device 100 is powered on, at step S302 the controller 2105 obtains capsule validation information (also sometimes referred to as capsule verification information or capsule authentication information) from the memory 2130. In at least one example, the capsule validation information may include a fusing profile (or fusing profile envelope), an expected fusing profile period (also sometimes referred to herein as the fusing profile period), and heater resistance parameters.

If the aerosol-generating device 100 is powered on when the capsule 200 is inserted, then the controller 2105 may determine that the capsule 200 has been inserted by obtaining a signal from via the one or more sensors configured to detect the lid opening and closure, which is discussed above with regard to FIGS. 1A-1D. In other example embodiments, the aerosol-generating device 100 may include a capsule detection switch (not shown). The capsule detection switch detects whether the capsule is properly inserted (e.g., capsule detection switch gets pushed down/closes when the capsule is properly inserted). Upon the capsule 200 being properly inserted, the controller 2105 may generate the signal PWR_EN_VGATE (shown in FIG. 7A) at a high level (e.g., logic high level). In addition, the controller 2105 may perform a heater continuity check to determine the capsule is inserted and the heater resistance is within the specified range (e.g. about ±20%).

The heater resistance parameters may include a nominal resistance parameter $R_{NOMINAL}$ of the heater 336, a short-circuit parameter and an open circuit parameter for the capsule 200.

As discussed above, the nominal resistance $R_{NOMINAL}$ refers to the resistance of the heater 336 with the fuse element 408 open circuited (or not present).

The short circuit parameter may be a short circuit resistance threshold $TH_{SC}$ for the heater system 36, and the open circuit parameter may be an open circuit resistance threshold $TH_{OC}$ for the heater system 36. The short circuit resistance threshold $TH_{SC}$ and the open circuit resistance threshold $TH_{OC}$ may be threshold parameters indicating whether the heater system 36 is within operational limits or tolerances and not faulty, and thus, invalid. In one example, a faulty capsule may be damaged, mismanufactured, counterfeit, or the like. In one example, for a 0.10 Ohm fuse 408 and a 2.0 Ohm heater 336, the short circuit resistance threshold $TH_{SC}$ may be about 0.05 Ohms and the open circuit resistance threshold $TH_{OC}$ may be about 0.15 Ohms.

In another example, for a 2.0 Ohm heater 336 and 2.0 Ohm fuse 408, the short circuit resistance threshold $TH_{SC}$ may be about 0.5 Ohms and the open circuit resistance threshold $TH_{OC}$ may be about 1.5 Ohms.

The fusing profile may include a defined power profile (or waveform) to be applied to the heater system 36 for validating the capsule 200 and an expected resistance profile (or expected resistance profile envelope) expected to be observed or measured in response to application of the power profile to the heater system 36. The expected resistance profile may be defined as an upper and lower resistance bound at each 1 millisecond (ms) time step or 'tick' of the fusing profile period. The upper and lower resistance bounds at each 1 ms tick may be set as desired based on, for example, empirical evidence or testing results obtained based on known authentic, undamaged and/or not previously heated capsules. In another example, the upper and lower resistance bounds (limits of resistance) may be calculated based on the predicted manufacturing tolerance(s) for the heater 336 and fuse 408.

The expected fusing profile period obtained from the memory 2130 is an expected length of time during which the power profile is applied to the heater system 36 to determine whether the capsule 200 is valid. In one example, the fusing profile period may be between about 5 ms and about 400 ms or more. The time between each 1 ms tick may be referred to as a fusing (or resistance) profile interval, and the expected resistance profile may include a plurality of (e.g., between about 5 and about 500 or more) resistance profile intervals. An example power profile and corresponding example recorded resistance profiles will be discussed in more detail later with regard to FIGS. 11-13.

At step S304, the controller 2105 applies the power profile obtained at step S302 to the heating engine control circuit 2127, which in turn applies a corresponding power profile to the heater system 36 between terminals 402 and 404.

Also at step S304, upon application of the power profile to the heater system 36, the controller 2105 begins to monitor the power applied to the heater system 36, and measure and record the resistance across the heater system 36 at each 1 ms tick (time step). The controller 2105 may measure the resistance at each 1 ms time step based on a measured voltage and current across the heater system 36 according to the well-known equation R=V/I. The measured current and voltage across the heater system 36 may be provided by, or determined based on information provided by, the heater current measurement circuit 21258 and the heater voltage measurement circuit 21252, respectively.

At step S306, the controller 2105 determines whether the instantaneous resistance $R_0$ of the heater system 36 at time $t_0$ (the initial resistance of the heater system 36) is greater than or equal to the short circuit resistance threshold $TH_{SC}$, but less than or equal to the open circuit resistance threshold $TH_{OC}$, obtained at step S302.

If the controller 2105 determines that the instantaneous resistance $R_0$ is outside the bounds of the short circuit resistance threshold $TH_{SC}$ and the open circuit resistance threshold $TH_{OC}$ (less than the short circuit resistance threshold $TH_{SC}$ or greater than the open circuit resistance threshold $TH_{OC}$), then at step S322 the controller 2105 determines that the capsule 200 is invalid (e.g., faulty), and outputs a fault indication via the aerosol indicators 2135 (e.g., via a message displayed on the communication screen 140). In one example, the fault indication may be in the form of a sound, visual display and/or haptic feedback. For example, the indication may be a blinking red LED, a software message containing an error code that is sent (e.g., via Bluetooth) to a connected "App" on a remote electronic device, which may subsequently trigger a notification in the App, any combination thereof, or the like. In this instance, the controller 2105 also terminates application of power to the heater system 36 upon detecting that the capsule 200 is invalid.

Returning to step S306, if the controller 2105 determines that the instantaneous resistance $R_0$ is within the bounds of the short circuit resistance threshold $TH_{SC}$ and the open circuit resistance threshold $TH_{OC}$ (greater than or equal to the short circuit resistance threshold $TH_{SC}$ and less than or equal to the open circuit resistance threshold $TH_{OC}$), then at step S308 the controller 2105 determines whether the instantaneous resistance $R_0$ approximates the nominal resistance $R_{NOMINAL}$ for the heater 336. In one example, the instantaneous resistance $R_0$ may be considered an approximation of the nominal resistance $R_{NOMINAL}$ if the instantaneous resistance $R_0$ is within a tolerance band of about 10% of the nominal resistance $R_{NOMINAL}$. Whether the instantaneous resistance $R_0$ approximates the nominal resistance $R_{NOMINAL}$ of the heater 336 indicates whether the fuse element 408 is blown (open circuit) or altogether missing from the heater system 36, which indicates that the capsule 200 is invalid (e.g., a faulty heater or that the power has been previously applied to the heater system 36 to generate aerosol).

If the controller 2105 determines that the instantaneous resistance $R_0$ approximates the nominal resistance $R_{NOMINAL}$, then controller 2105 determines that the capsule is invalid (e.g., the fuse element 408 is open circuit and/or power has been previously applied to the heater system 36 to generate aerosol). In this case, the process proceeds to step S322 and continues as discussed above, including terminating application of power to the heater system 36.

Returning to step S308, if the controller 2105 determines that the instantaneous resistance $R_0$ does not approximate the nominal resistance $R_{NOMINAL}$, then the controller 2105 determines that the fuse element 408 is present and intact. In this case, the process continues to step S310 at which the controller 2015 causes (or allows) the heating engine control circuit 2127 to continue to apply power to the heater system 36 according to the power profile while concurrently recording the measured resistance across the heater system 36 at each 1 ms tick.

At step S314, at the next (e.g., first) 1 ms tick, the controller 2105 checks (e.g., via comparison) whether the measured resistance $R_{SYSTEM}$ of the heater system 36 has reached (e.g., is equal or substantially equal to) the nominal resistance $R_{NOMINAL}$ (with a correction offset or delta to account for heating effects). An example correction offset (dynamic correction) will be described below. However, it should be understood that the correction offset may be computed in any suitable manner.

When applying power during the fusing profile period, a portion of the energy heats the heater 336, thereby changing the temperature and consequently the resistance of the heater 336. A correction offset in the form of a resistance correction offset may be used to account for this heating effect.

For relatively low energy fusing profiles (e.g., fusing provides with relatively low power and/or relatively short duration of application), the extraneous heating of the heater 336 may be negligible and the change in (e.g., additional) resistance may be discounted. In this case, no correction offset is required since the nominal resistance $R_{NOMINAL}$ still lies within the permitted tolerance range defined in the resistance envelope.

For longer power profiles (e.g., greater than or equal to about 100 ms), or for power profiles that utilize relatively high power (e.g., greater than or equal to about 10 W), the heating effect on resistance may be more significant. In this case, the correction offset may be applied to the measured resistance (or, alternatively, to the resistance envelope) to ensure that the resistance is fairly compared to the envelope (e.g., to reduce false detections).

According to at least some example embodiments, the controller 2105 may calculate the correction offset (also referred to as a correction factor) algorithmically or using a look up table (LUT).

With regard to an example algorithmic calculation, the controller 2105 may calculate the correction offset by calculating the heating energy in Joules applied during the elapsed period of the heating profile, and then estimating the temperature rise induced in the heater 336 based on the heating energy (e.g., through a-priori knowledge of the mass of material in the heater 336 and the specific heat capacity associated therewith). The controller 2105 may then use this estimated temperature rise with a-priori knowledge of the Temperature Coefficient of Resistance of the heater 336 to calculate the increase in resistance at each point in time (the correction offset). For increased accuracy, the proportion of heating energy applied to the fuse 408 and applied to the heater 336 may be apportioned based on a-priori knowledge of the starting resistance of these elements.

In an example utilizing a LUT, the controller 2105 may calculate the correction offset by calculating the heating energy in Joules applied to the heater system 36, and then apportioning a fraction of that to the heater 336 based on a percentage field stored within the resistance envelope. In this case, the resistance envelope is defined as a LUT, rather than algorithmically. Alternatively, the controller 2105 may utilize a dedicated LUT.

In both the algorithmic and LUT examples, the controller 2105 may calculate the heating energy in Joules by measuring the actual power delivered to the capsule (as opposed to the power specified in the fusing profile waveform), and then integrating the measured power for the time during which each power level is applied. This may enable improved accuracy by more accurately accounting for the actual power delivery, which may be more or less than the specified power delivery due to system variations.

In one example, for a 2.0 Ohm stainless steel heater 336 of mass 0.075 g heated with an apportioned power profile of 12 W for 400 ms, the resistance increase is approximately 200 mOhm. The correction offset added to the nominal resistance $R_{NOMINAL}$ (or to the resistance envelope) at point 400 ms in the power profile is therefore 200 mOhm.

According to at least some example embodiments, the correction offset may also be used to inform subsequent resistance based temperature control by using the calculated temperature rise at the end of the fusing profile as the starting point for temperature control (e.g., heater starting temperature=ambient temperature+temperature rise). However, this may also be managed by enforcing a waiting period after the completion of the fusing profile before the adult consumer may operate the product to allow the heater 336 to cool down to ambient temperature.

Still referring to FIG. 9, if the controller 2105 determines that the resistance $R_{system}$ of the heater system 36 has not yet reached the nominal resistance $R_{NOMINAL}$, which indicates that the fuse element 408 is still intact (not blown), then at step S312 the controller 2105 determines whether the expected fusing profile period has expired.

If the controller 2105 determines that the expected fusing profile period has not yet expired, then the process returns to step S314 at which the controller 2105 rechecks whether the resistance of the heater system 36 has reached the nominal resistance $R_{NOMINAL}$ at the next 1 ms tick. The process then continues as discussed herein. According to one or more example embodiments, the controller 2105 may check and recheck whether the resistance of the heater system 36 has reached the nominal resistance $R_{NOMINAL}$ periodically at each 1 ms tick. Although discussed herein with regard to a 1 ms periodicity, example embodiments should not be limited to this example.

Returning to step S312, if the expected fusing profile period has expired (e.g., without the resistance of the heater system 36 reaching the nominal resistance $R_{NOMINAL}$), then at step S316 the controller 2105 terminates application of power to the heater system 36.

At step S318, the controller 2105 determines whether the recorded resistance profile for the heater system 36 during the expected fusing profile period is within the bounds of the expected resistance profile obtained from the memory at step S302. In one example, the controller 2105 compares the recorded resistance profile with the expected resistance profile (defined as an upper and lower resistance bound at each 1 ms tick) to determine whether the recorded resistance value at each 1 ms tick is within the bounds of the expected resistance profile at the corresponding point in the expected resistance profile. According to example embodiments, the expected resistance profile may be interpolated or decimated as needed to match the length of the recorded resistance profile, depending on whether the application of the power profile was terminated prior to expiration of the fusing profile period.

If the controller 2105 determines that the recorded resistance profile is not within the bounds of the expected resistance profile, then the process proceeds to step S322 at which a fault indication is output as discussed above.

Returning to step S318, if the controller 2105 determines that the recorded resistance profile is within the bounds of the expected resistance profile, then at step S320 the controller 2105 determines that the capsule is valid and enables application of power to the heater system 36 to generate aerosol. When the heater system 36 is activated (e.g., so as to undergo Joule heating), the temperature of the aerosol-forming substrate may increase, and an aerosol may be generated and drawn or otherwise released through the aerosol outlets of the capsule 200.

Returning to step S314, if the controller 2105 determines that the resistance of the heater system 36 has reached the nominal resistance $R_{NOMINAL}$ at any 1 ms tick (indicating that the fuse element 408 has blown), then the process continues to step S316 and proceeds as discussed herein. In this case, the controller 2105 may terminate application of the power profile to the heater system 36 prior to expiration of the expected fusing profile period, and decimate the expected resistance profile envelope according to the length of time the power profile was applied to the heater system 36.

Once aerosol generation is permitted, the controller 2105 may estimate the starting temperature $T_0$ of the heater 336 by estimating the proportion of the power profile delivered to the heater system 36 during the validation procedure discussed above. In this case, the initial resistance $R_0$ of the heater 336 for heating is set to the final resistance of the heater 336 according to the recorded resistance profile.

According to at least one example embodiment, the controller 2105 may estimate the starting temperature $T_0$ of the heater 336 using the final resistance of the heater system 36 at the end of the recorded resistance profile as discussed above with regard to FIG. 9. In one example, the controller 2105 may compute the starting temperature $T_0$ of the heater 336 based on the last recorded resistance prior to the end of the expected fusing profile period at time $t_{end}$. In another example, if the controller 2105 terminates application of power to the heater system 36 prior to the end of the expected fusing profile period, then the controller 2105 may compute the starting temperature $T_0$ of the heater 336 based on the recorded resistance at the last 1 ms tick prior to termination of the application of power to the heater system 36. An example method for computing the starting temperature $T_0$ will be discussed below. However, example embodiments should not be limited to this example. Rather, according to example embodiments, the controller 2105 may compute the starting temperature $T_0$ based on resistance in any known manner.

In more detail, according to one or more example embodiments, the controller 2105 may estimate the starting temperature $T_0$ by estimating the amount of energy (e.g., number of Joules) injected into the heater 336 during the fusing profile. The controller 2105 may compute this estimate algorithmically or by appending an extra column/field to the fusing profile that apportions the number and/or fraction of the amount of energy (e.g., Joules) injected to the heater 336.

The algorithmic calculation, or a summation of the fusing profile 'Joules' field, may then be used to calculate the amount of energy (e.g., in number of Joules) that were injected into the heater 336. The temperature rise of the heater 336 (and therefore starting temperature $T_0$) may then be calculated using a-priori knowledge of the approximate heater mass.

In another example, a cooldown period (e.g., a few seconds) may be enforced before permitting the adult consumer to operate the device. This allows the heater 336 to cool (e.g., to ambient temperature) so that the initial resistance $R_0$ and the starting temperature $T_0$ may be estimated using traditional temperature controlled vaping techniques.

For systems that have relatively low fuse resistances (e.g., $R_{fuse}$ less than about 10% of $R_{heater}$), the resistance $R_{system}$ of the heater system 36 may be relatively low. In this case, the short circuit resistance threshold $TH_{SC}$ and the open circuit resistance threshold $TH_{OC}$ may be more difficult to measure. Consequently, although shown in FIG. 9, according to one or more example embodiments, step S306 may be omitted. In this case, the process may proceed from step S304 to step S308.

Figure 10:
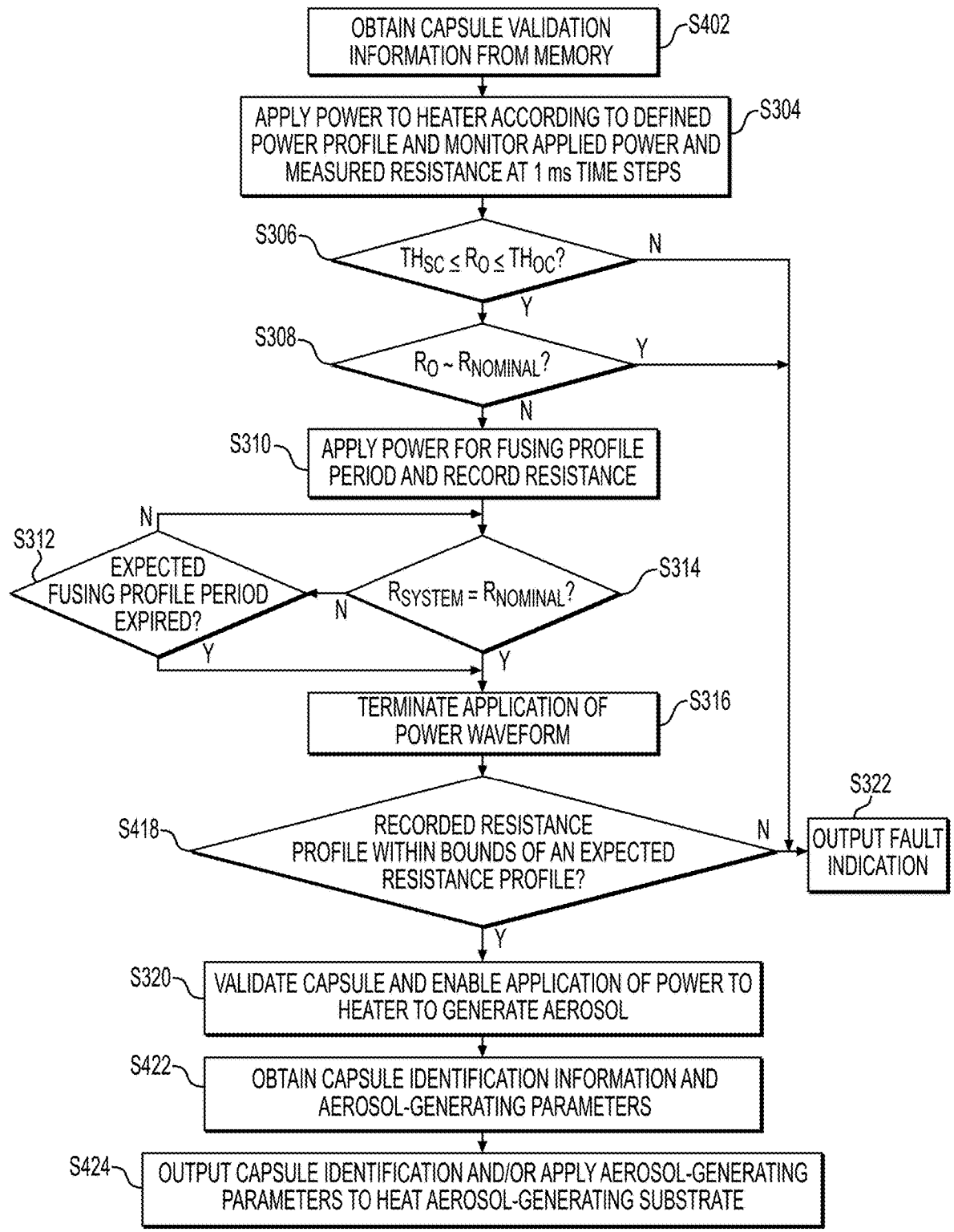
FIG. 10 is a flow chart illustrating another method of controlling an aerosol-generating device according to at least some example embodiments.

FIG. 10 is a flow chart for validating and identifying a capsule inserted into the device body according to example embodiments. For example purposes, the flow chart shown in FIG. 10 will be discussed with regard to the devices and electrical systems described herein. It should be understood, however, that example embodiments should not be limited to these examples. Rather, example embodiments may be applicable to other aerosol-generating devices and electrical systems thereof. Moreover, the example embodiment shown in FIG. 10 will be described with regard to operations performed by the controller 2105. However, example embodiments should not be limited to this example.

The example embodiment shown in FIG. 10 may be performed to detect and/or determine whether a capsule inserted into the aerosol-generating device is valid, and to identify the type of capsule inserted into the aerosol-generating device. By identifying the type of capsule inserted, the aerosol-generating device may output identification information via the aerosol indicators 2135 and/or utilize heating parameters to adjust heating of the aerosol-forming substrate included in the capsule 200.

Referring to FIG. 10, when the capsule 200 is inserted into the aerosol-generating device 100, and the aerosol-generating device is powered on, at step S402 the controller 2105 obtains capsule validation information from the memory 2130. The capsule validation information may be similar to the capsule validation information discussed above with regard to step S302 in FIG. 9, but may include a defined power profile, fusing profile period, and a plurality of expected resistance profiles.

Each of the expected resistance profiles may have different characteristics (e.g., different upper and lower bounds at each 1 ms tick, etc.).

According to at least this example embodiment, each of the plurality of expected resistance profiles may be stored in association with capsule identification information and corresponding aerosol-generating parameters in, for example, a LUT in the memory 2130. The capsule identification information may include one or more of information indicative of a type or blend of the aerosol-forming substrate in the capsule, a capsule type, manufacturing information (e.g., manufacture date, location, etc.), a SKU for the capsule, or the like. The aerosol generating parameters may include parameters such as a heating power profile, a target temperature and/or a target resistance for heating the aerosol-forming substrate in the capsule to generate aerosol.

At step S304, the controller 2105 applies the defined power profile to the heater system 36 in the same or substantially the same manner as discussed above with regard to FIG. 9. The controller 2105 also begins to monitor the power applied to the heater system 36 and record the measured resistance of the heater system 36 at 1 ms time steps in the same or substantially the same manner as discussed above with regard to FIG. 9.

At step S306, the controller 2105 determines whether the instantaneous resistance $R_0$ of the heater system 36 is within the bounds of the short circuit resistance threshold $TH_{SC}$ and the open circuit resistance threshold $TH_{OC}$ in the same or substantially the same manner as discussed above with regard to FIG. 9.

If the controller 2105 determines that the instantaneous resistance $R_0$ is outside of the bounds of the short circuit resistance threshold $TH_{SC}$ and the open circuit resistance threshold $TH_{OC}$, then the process proceeds to step S322 and continues as discussed above with regard to FIG. 9.

Returning to step S306, if the controller 2105 determines that the instantaneous resistance $R_0$ is within the bounds of the short circuit resistance threshold $TH_{SC}$ and the open circuit resistance threshold $TH_{OC}$, then at step S308 the controller 2105 determines whether the instantaneous resistance $R_0$ approximates the nominal resistance $R_{NOMINAL}$ in the same or substantially the same manner as discussed above with regard to FIG. 9.

If the controller 2105 determines that the instantaneous resistance $R_0$ approximates the nominal resistance $R_{NOMINAL}$, then the process proceeds to step S322 and continues as discussed above with regard to FIG. 9.

Returning to step S308, if the controller 2105 determines that the instantaneous resistance $R_0$ does not approximate the nominal resistance $R_{NOMINAL}$, then at step S310 the controller 2015 causes the heating engine control circuit 2127 to continue to apply the power waveform to the heater system 36 as discussed above with regard to FIG. 9.

At step S314, at the next (e.g., first) 1 ms tick, the controller 2105 checks (e.g., via comparison) whether the measured resistance of the heater system 36 has reached (e.g., is equal or substantially equal to) the nominal resistance $R_{NOMINAL}$ (with a correction offset or delta to account for heating effects) in the same or substantially the same manner as discussed above with regard to FIG. 9.

If the controller 2105 determines that the resistance of the heater system 36 has not reached the nominal resistance $R_{NOMINAL}$, then at step S312 the controller 2105 determines whether the expected fusing profile period has expired.

If the controller 2105 determines that the expected fusing profile period has not yet expired, then the process returns to step S314, at which the controller 2105 rechecks whether the resistance of the heater system 36 has reached the nominal resistance $R_{NOMINAL}$ at the next 1 ms tick. The process then continues as discussed herein.

As with the example embodiment shown in FIG. 9, in the example embodiment shown in FIG. 10, the controller 2105 may check and recheck whether the resistance of the heater system 36 has reached the nominal resistance $R_{NOMINAL}$ periodically at each 1 ms tick. Moreover, although discussed herein with regard to a 1 ms periodicity, example embodiments should not be limited to this example.

Returning to step S312, if the expected fusing profile period has expired, then at step S316 the controller 2105 terminates application of power to the heater system 36 as discussed above with regard to FIG. 9.

At step S418, the controller 2105 determines whether the recorded resistance profile for the heater system 36 is within the bounds of an expected resistance profile among the plurality of expected resistance profiles obtained from the memory 2130 at step S402. In one example, the controller 2105 compares the recorded resistance profile with each respective one of the plurality of expected resistance profiles to determine whether the recorded resistance value at each 1 ms tick is within the bounds of the respective expected resistance profile at the corresponding point in the profile. As with the example embodiment shown in FIG. 9, according to example embodiments, the expected resistance profile may be interpolated or decimated as needed to match the length of the recorded resistance profile. For simplicity, a recorded resistance profile that is within the bounds of an expected resistance profile is described herein as "matching" that expected resistance profile.

If the controller 2105 determines that the recorded resistance profile does not match any of the plurality of expected resistance profiles, then the process proceeds to step S322 at which a fault indication is output as discussed herein.

Returning to step S418, if the controller 2105 determines that the recorded resistance profile matches an expected resistance profile among the plurality of expected resistance profiles, then at step S320 the controller 2105 determines that the capsule is valid and enables application of power to the heater system 36 to generate aerosol as discussed above with regard to FIG. 9.

At step S422, the controller 2105 obtains capsule identification information and/or aerosol-generating parameters for the capsule 200 based on the matching expected resistance profile. In one example, the controller 2105 obtains the capsule identification information and/or aerosol-generating parameters by accessing the above-discussed LUT in the memory 2130 to obtain the identification information and/or aerosol-generating parameters stored in association with the matching expected resistance profile. As mentioned above, the capsule identification information may include one or more of information indicative of a type or blend of the aerosol-forming substrate in the capsule, a capsule type, manufacturing information (e.g., manufacture date, location, etc.), a SKU for the capsule, or the like. The aerosol generating parameters may include parameters such as a heating power profile, a target temperature and/or a target resistance for heating the aerosol-forming substrate in the capsule to generate aerosol.

Still referring to FIG. 10, at step S424 the controller 2105 outputs at least a portion of the obtained capsule identification information for the capsule via the aerosol indicators 2135 (e.g., via the communication screen 140). In one example, the controller 2105 may output the capsule identification information as a software message sent (e.g., via Bluetooth) to a connected "App" on a remote electronic device, which may subsequently trigger a notification in the App. Also at step S424, the controller 2105 may apply the aerosol-generating parameters when heating the aerosol-forming substrate to generate aerosol.

Returning to step S314, if the controller 2105 determines that the resistance of the heater system 36 has reached the nominal resistance $R_{NOMINAL}$, then the process continues to step S316 and proceeds as discussed herein.

Once aerosol generation is permitted, the controller 2105 may estimate the starting temperature $T_0$ of the heater system 36 by estimating the proportion of the power profile delivered to the heater system 36 in the same or substantially the same manner as discussed above with regard to the example embodiment shown in FIG. 9.

As with the example embodiment shown in FIG. 9, although step S306 is shown in FIG. 10, according to one or more example embodiments, step S306 may be omitted. In this case, the process may proceed from step S304 to step S308.

FIGS. 11-13 are graphs illustrating example power profiles and corresponding recorded resistance profiles according to example embodiments. FIG. 11 is a graph illustrating a power profile and corresponding recorded resistance profile for an authentic capsule of a first type having a heater resistance of about 2 Ohms ($R_{heater}$=2Ω) and a fuse element resistance of about 0.01 Ohms ($R_{fuse}$=0.01Ω). FIG. 12 is a graph illustrating a power profile and corresponding recorded resistance profile for a counterfeit capsule having a heater resistance of about 2 Ohms ($R_{heater}$=2Ω) and a fuse element resistance of about 0.01 Ohms ($R_{fuse}$=0.01Ω). FIG. 13 is a graph illustrating a power profile and corresponding recorded resistance profile for an authentic capsule of a second type having a heater resistance of about 2 Ohms ($R_{heater}$=2Ω) and a fuse element resistance of about 0.04 Ohms ($R_{fuse}$=0.04Ω). In each of FIGS. 11-13, the power profile is the same and the fusing profile period is about 400 ms ($t_{end}$=400 ms). For example purposes, the graphs shown in FIGS. 11-13 will be discussed with regard to the heater system 36 shown in FIG. 2D.

Referring to FIG. 11, the resistance characteristics of the heater system 36 including the fuse element 408 in parallel with the heater 336 are non-linear based on the heating effect on the fuse element 408 that causes the resistance $R_{fuse}$ of the fuse element 408 to change more significantly than the resistance $R_{heater}$ of the heater 336. The difference in resistance characteristics in the fuse element 408 and the heater 336 are indicative of the ratio of resistances and the differences in the mass of material of the fuse element 408 relative to the heater 336 (the mass of material in the fuse element<<the mass of material in the heater).

The resistance $R_{system}$ of the heater system 36 increases as a result of both the resistance $R_{fuse}$ of the fuse element 408 and the resistance $R_{heater}$ of the heater 336 until a fracture point at time t-fracture, wherein the fuse element 408 is open-circuited (blown). After the fracture point at time t-fracture, the resistance $R_{system}$ of the heater system 36 is equal to the resistance of the heater $R_{heater}$ ($R_{system}$=$R_{heater}$), and subsequent changes to the recorded resistance profile are a result of temperature increases in the heater 336. In the example shown in FIG. 11, the fracture point occurs about 160 ms after initial application of the power profile to the heater system (t-fracture=~160 ms).

Once the fracture point has been reached, the controller 2105 may terminate application of the power profile to the heater system 36 at any time to minimize joule heating of the heater 336. In instances where the controller 2105 terminates application of the power profile prior to expiration of the expected fusing profile period, the controller 2105 may decimate the expected resistance profile to match the length of the actual fusing profile period.

If the controller 2105 does not terminate application of the power profile prior to expiration of the expected fusing profile period, then the application of the power profile is terminated at the end of the expected fusing profile period (after about 400 ms), and the heater 336 begins to cool down.

As noted above, FIG. 12 is a graph illustrating a power profile and corresponding recorded resistance profile for a counterfeit (invalid) capsule having a heater resistance of about 2 Ohms ($R_{heater}=2\Omega$) and a fuse element resistance of about 0.01 Ohms ($R_{fuse}=0.01\Omega$). The graph in FIG. 12 is similar to the graph shown in FIG. 11, and thus, the discussion of this figure will focus on the differences between FIGS. 11 and 12.

As compared to the graph shown in FIG. 11, the resistance characteristic of the heater system 36 in FIG. 12 is different. In this example, the value of the resistance $R_{fuse}$ of the fuse element 408 may be similar to that in FIG. 11, but the volume of material in the fuse element is different because the capsule is not authentic (e.g., poorly or improperly manufactured by a third party or suffering from manufacturing defects). As a result, the heating effect, and therefore the resistance profile of the heater system 36 in response to application of the power profile, is different.

The additional mass of material of the fuse element 408 prevents the pinched region from reaching its melting point (e.g., about 1400° C. for SS316L) and does not fracture (open circuit) as with the example shown in FIG. 11. Thus, in contrast to the example shown in FIG. 11, there is no fracture point in the recorded resistance profile shown in FIG. 12.

As noted above, FIG. 13 is a graph illustrating a power profile and corresponding recorded resistance profile for an authentic capsule of a second type having a heater resistance of about 2 Ohms ($R_{heater}=2\Omega$) and a fuse element resistance of about 0.04 Ohms ($R_{fuse}=0.04\Omega$). The graph in FIG. 13 is similar to the graph shown in FIG. 11, and thus, the discussion of this figure will focus on the differences between FIGS. 11 and 13.

Similar to FIG. 11, in the example shown in FIG. 13, the resistance of the heater system increases nonlinearly until reaching a fracture point at time $t_{fracture}$.

After the fracture point at time $t_{fracture}$, the resistance $R_{system}$ of the heater system 36 is equal to the resistance $R_{heater}$ of the heater 336 ($R_{system}=R_{heater}$), and subsequent changes to the recorded resistance profile are a result of temperature increases in the heater 336. In the example shown in FIG. 13, the fracture point occurs about 90 ms after initial application of the power profile to the heater system 36 ($t_{fracture}=\sim 90$ ms).

In the example shown in FIG. 13, the lower resistance (and therefore mass) of the fuse element 408, relative to that discussed above with regard to FIG. 11, causes the resistance to increase more rapidly, which results in an earlier fracture point relative to the fracture point shown in FIG. 11.

One or more example embodiments may provide a relatively low cost manner in which to authenticate and/or validate a capsule, thereby determining whether a capsule is authentic or counterfeit. If a counterfeit capsule is detected, then the aerosol-generating device may prevent application of power to the heater.

One or more example embodiments may provide a relatively low cost manner in which to determine whether an aerosol-forming substrate in a capsule has been heated previously, thereby mitigating the possibility that power is applied to a depleted capsule.

One or more example embodiments may decrease costs associated with the aerosol-generating devices, including the capsules, since the aerosol-generating device need not include dedicated electronics (e.g., a programmable read-only memory (PROM)) for authentication and quality control.

One or more example embodiments may improve sensory experience by preventing use of unauthorized, previously heated or counterfeit capsules that deliver relatively poor vaping experience.

As discussed herein, an aerosol-forming substrate is a material or combination of materials that may yield an aerosol. An aerosol relates to the matter generated or output by the devices disclosed, claimed, and equivalents thereof. The material may include a compound (e.g., nicotine, cannabinoid), wherein an aerosol including the compound is produced when the material is heated.

It is understood that heating of a plant material below its ignition temperature may, in some circumstances, produce incidental and insubstantial levels of oxidized or other thermal decomposition byproducts. However, in some embodiments, the heating in aerosol-generating devices is below the pyrolysis temperature of the plant material so as to produce an aerosol having no or insubstantial levels of thermal decomposition byproducts of the plant material. Thus, in an example embodiment, pyrolysis of the plant material does not occur during the heating and resulting production of aerosol. In other instances, there may be incidental pyrolysis, with production of oxidized or other thermal decomposition byproducts at levels that are insignificant relative to the primary constituents released by heating of the plant materials.

The aerosol-forming substrate may be a fibrous material. For instance, the fibrous material may be a botanical material. The fibrous material is configured to release a compound when heated. The compound may be a naturally occurring constituent of the fibrous material. For instance, the fibrous material may be plant material such as tobacco, and the compound released may be nicotine. The term "tobacco" includes any tobacco plant material including tobacco leaf, tobacco plug, reconstituted tobacco, compressed tobacco, shaped tobacco, or powder tobacco, and combinations thereof from one or more species of tobacco plants, such as *Nicotiana rustica* and *Nicotiana tabacum*.

In some example embodiments, the tobacco material may include material from any member of the genus *Nicotiana*. In addition, the tobacco material may include a blend of two or more different tobacco varieties. Examples of suitable types of tobacco materials that may be used include, but are not limited to, flue-cured tobacco, Burley tobacco, Dark tobacco, Maryland tobacco, Oriental tobacco, rare tobacco, specialty tobacco, blends thereof, and the like. The tobacco material may be provided in any suitable form, including, but not limited to, tobacco lamina, processed tobacco materials, such as volume expanded or puffed tobacco, processed tobacco stems, such as cut-rolled or cut-puffed stems, reconstituted tobacco materials, blends thereof, and the like. In some example embodiments, the tobacco material is in the form of a substantially dry tobacco mass. Furthermore, in some instances, the tobacco material may be mixed and/or combined with at least one of propylene glycol, glycerin, sub-combinations thereof, or combinations thereof.

The compound may also be a naturally occurring constituent of a medicinal plant that has a medically-accepted therapeutic effect. For instance, the medicinal plant may be a *cannabis* plant, and the compound may be a cannabinoid. Cannabinoids interact with receptors in the body to produce a wide range of effects. As a result, cannabinoids have been used for a variety of medicinal purposes (e.g., treatment of pain, nausea, epilepsy, psychiatric disorders). The fibrous material may include the leaf and/or flower material from one or more species of *cannabis* plants such as *Cannabis sativa*, *Cannabis indica*, and *Cannabis ruderalis*. In some instances, the fibrous material is a mixture of 60-80% (e.g., 70%) *Cannabis sativa* and 20-40% (e.g., 30%) *Cannabis indica*.

Examples of cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (THCA) and cannabidiolic acid (CBDA) may be converted to tetrahydrocannabinol (THC) and cannabidiol (CBD), respectively, via heating. In an example embodiment, heat from a heater (e.g., heater 336) may cause decarboxylation so as to convert the tetrahydrocannabinolic acid (THCA) in the capsule 200 to tetrahydrocannabinol (THC), and/or to convert the cannabidiolic acid (CBDA) in the capsule 200 to cannabidiol (CBD).

In instances where both tetrahydrocannabinolic acid (THCA) and tetrahydrocannabinol (THC) are present in the capsule 200, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC) during the heating of the capsule 200. Similarly, in instances where both cannabidiolic acid (CBDA) and cannabidiol (CBD) are present in the capsule 200, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD) during the heating of the capsule 200.

Furthermore, the compound may be or may additionally include a non-naturally occurring additive that is subsequently introduced into the fibrous material. In one instance, the fibrous material may include at least one of cotton, polyethylene, polyester, rayon, combinations thereof, or the like (e.g., in a form of a gauze). In another instance, the fibrous material may be a cellulose material (e.g., non-tobacco and/or non-*cannabis* material). In either instance, the compound introduced may include nicotine, cannabinoids, and/or flavorants. The flavorants may be from natural sources, such as plant extracts (e.g., tobacco extract, *cannabis* extract), and/or artificial sources. In yet another instance, when the fibrous material includes tobacco and/or *cannabis*, the compound may be or may additionally include one or more flavorants (e.g., menthol, mint, vanilla). Thus, the compound within the aerosol-forming substrate may include naturally occurring constituents and/or non-naturally occurring additives. In this regard, it should be understood that existing levels of the naturally occurring constituents of the aerosol-forming substrate may be increased through supplementation. For example, the existing levels of nicotine in a quantity of tobacco may be increased through supplementation with an extract containing nicotine. Similarly, the existing levels of one or more cannabinoids in a quantity of *cannabis* may be increased through supplementation with an extract containing such cannabinoids.

Further to the non-limiting embodiments set forth herein, additional details of the substrates, capsules, devices, and methods discussed herein may also be found in U.S. application Ser. No. 16/451,662, filed Jun. 25, 2019, titled "CAPSULES, HEAT-NOT-BURN (HNB) AEROSOL-GENERATING DEVICES, AND METHODS OF GENERATING AN AEROSOL,"; U.S. application Ser. No. 16/252,951, filed Jan. 21, 2019, titled "CAPSULES, HEAT-NOT-BURN (HNB) AEROSOL-GENERATING DEVICES, AND METHODS OF GENERATING AN AEROSOL,"; U.S. application Ser. No. 15/845,501, filed Dec. 18, 2017, titled "VAPORIZING DEVICES AND METHODS FOR DELIVERING A COMPOUND USING THE SAME,"; and U.S. application Ser. No. 15/559,308, filed Sep. 18, 2017, titled "VAPORIZER FOR VAPORIZING AN ACTIVE INGREDIENT,", the disclosures of each of which are incorporated herein in their entirety by reference.

While a number of example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

What is claimed is:

1. A heater system for a non-combustible aerosol-generating device, the heater system comprising:
   a heater element having a heating region, a first terminal and a second terminal;
   a fuse element electrically connected between the first terminal and the second terminal in parallel with the heater element, the fuse element having a region configured to induce a localized hot spot to cause the fuse element to open circuit in response to power applied between the first terminal and the second terminal; and
   an end cap having a chamber configured to isolate the fuse element from air flow through the heater system.

2. The heater system of claim 1, wherein the fuse element has a resistance enabling a heating power required to activate the fuse element to be passed through the heater system.

3. The heater system of claim 1, wherein the region configured to induce a localized hot spot is a pinched or necked region.

4. The heater system of claim 1, wherein the fuse element is ultrasonically, electrically or laser spot welded between the first terminal and the second terminal.

5. The heater system of claim 1, wherein the fuse element is integral with the heater element.

6. The heater system of claim 1, wherein
   the heater element includes
      a first extension region connecting the heating region with the first terminal, and
      a second extension region connecting the heating region with the second terminal; and
   the fuse element is electrically connected to the first extension region and the second extension region.

7. A capsule of a non-combustible aerosol-generating device, the capsule comprising:
   a housing containing an aerosol-forming substrate, the housing having a first end cap;
   a heater element arranged within the housing, the heater element having a first terminal, a second terminal and a heating region configured to heat the aerosol-forming substrate; and
   a fuse element electrically connected in parallel with the heater element, the fuse element having a region configured to induce a localized hot spot to cause the fuse element to open circuit in response to power applied between the first terminal and the second terminal, the first end cap including a chamber configured to isolate the fuse element from air flow through the capsule.

8. The capsule of claim 7, wherein the fuse element has a resistance enabling a heating power required to activate the fuse element to be passed through the heater element and the fuse element.

9. The capsule of claim 7, wherein the region configured to induce a localized hot spot is a pinched or necked region.

10. The capsule of claim 7, wherein the fuse element is ultrasonically, electrically or laser spot welded between the first terminal and the second terminal.

11. The capsule of claim 7, wherein the fuse element is integral with the heater element.

12. The capsule of claim 7, wherein the housing comprises:
 a sleeve having a first end and a second end; and
 a second end cap engaged with the second end, wherein
  the first end cap is engaged with the first end, and
  the first end cap is molded around the first terminal, the second terminal and the fuse element.

13. The capsule of claim 7, wherein
 the heater element includes
  a first extension region connecting the heating region with the first terminal, and
  a second extension region connecting the heating region with the second terminal; and
 the fuse element is electrically connected to the first extension region and the second extension region.

14. A non-combustible aerosol-generating device comprising:
 a capsule having an end cap, the capsule including
  a heater element having a first terminal, a second terminal and a heating region configured to heat an aerosol-forming substrate, and
  a fuse element electrically connected in parallel with the heater element, the fuse element having a region configured to induce a localized hot spot to cause the fuse element to open circuit in response to power applied between the first terminal and the second terminal, the end cap having a chamber configured to isolate the fuse element from air flow through the capsule; and a device body configured to connect to the capsule, the device body including
  a power supply to provide power to the non-combustible aerosol-generating device, and
  a controller configured to control application of power to the heater element.

15. A non-combustible aerosol-generating device comprising:
 a capsule including
  a housing containing an aerosol-forming substrate,
  a heater element arranged in the housing, the heater element having a first terminal, a second terminal and a heating region configured to heat the aerosol-forming substrate, and
  a fuse element electrically connected between the first terminal and the second terminal; and
 a device body configured to connect to the capsule, the device body including
  a heating engine control circuit configured to apply power to the heater element, and
  a controller configured to
   control the heating engine control circuit to apply a power waveform to the heater element, and
   determine whether the capsule is valid based on a measured resistance profile for the heater element in response to the power waveform.

16. The non-combustible aerosol-generating device of claim 15, further comprising:
 a memory storing an expected resistance profile; and wherein
 the controller is configured to determine whether the capsule is valid based on a comparison between the measured resistance profile and the expected resistance profile stored in the memory.

17. The non-combustible aerosol-generating device of claim 15, wherein the controller is configured to enable application of power to the heater element to heat the aerosol-forming substrate to generate aerosol in response to determining that the capsule is valid.

18. The non-combustible aerosol-generating device of claim 15, wherein the controller is configured to prevent application of power to the heater element to heat the aerosol-forming substrate to generate aerosol in response to determining that the capsule is not valid.

19. The non-combustible aerosol-generating device of claim 15, wherein the controller is configured to control the heating engine control circuit to apply the power waveform to the heater element, and to determine whether the capsule is valid prior to application of power to the heater element to heat the aerosol-forming substrate to generate aerosol.

20. The non-combustible aerosol-generating device of claim 15, wherein the controller is configured to obtain identification information for the capsule based on the measured resistance profile.

21. The non-combustible aerosol-generating device of claim 20, further comprising:
 a memory storing a plurality of expected resistance profiles; and wherein
 the controller is configured to obtain the identification information for the capsule based on a comparison between the measured resistance profile and the plurality of expected resistance profiles stored in the memory.

22. The non-combustible aerosol-generating device of claim 15, wherein the controller is configured to determine aerosol-generating parameters for heating the aerosol-forming substrate based on the measured resistance profile.

23. The non-combustible aerosol-generating device of claim 22, further comprising:
 a memory storing a plurality of expected resistance profiles; and wherein
 the controller is configured to determine the aerosol-generating parameters based on a comparison between the measured resistance profile and the plurality of expected resistance profiles stored in the memory.

24. The non-combustible aerosol-generating device of claim 22, wherein the aerosol-generating parameters include at least one of a heating power profile, a target temperature or a target resistance for heating the aerosol-forming substrate to generate aerosol.

25. The non-combustible aerosol-generating device of claim 15, wherein a valid capsule is at least one of an authentic capsule, a capsule that has not been damaged prior to insertion into the non-combustible aerosol-generating device, or a capsule having an intact fuse element.

* * * * *